(12) United States Patent
Bird et al.

(10) Patent No.: US 7,253,290 B2
(45) Date of Patent: Aug. 7, 2007

(54) PYRAZOLE DERIVATIVES AS GNRH INHIBITORS

(75) Inventors: Thomas Geoffrey Bird, Reims Cedex 2 (FR); Mickael Louis Pierre Maudet, Reims Cedex 2 (FR)

(73) Assignee: AstraZeneca AB, Södertalje (SE)

( * ) Notice: Subject to any disclaimer, the term of this patent is extended or adjusted under 35 U.S.C. 154(b) by 75 days.

(21) Appl. No.: 10/525,111

(22) PCT Filed: Aug. 19, 2003

(86) PCT No.: PCT/GB03/03623

§ 371 (c)(1),
(2), (4) Date: Feb. 18, 2005

(87) PCT Pub. No.: WO2004/018459

PCT Pub. Date: Mar. 4, 2004

(65) Prior Publication Data

US 2005/0239858 A1 Oct. 27, 2005

(30) Foreign Application Priority Data

Aug. 21, 2002 (EP) .................................. 02292075

(51) Int. Cl.
*C07D 401/14* (2006.01)
*C07D 403/12* (2006.01)
(52) U.S. Cl. ................... 548/370.1; 514/404; 514/339; 514/341; 548/364.1; 546/276.1
(58) Field of Classification Search ............ 548/370.1
See application file for complete search history.

(56) References Cited

FOREIGN PATENT DOCUMENTS

| WO | WO 97/21435 A1 | 6/1997 |
|---|---|---|
| WO | WO 97/21703 A1 | 6/1997 |
| WO | WO 97/21704 A1 | 6/1997 |
| WO | WO 97/21707 A1 | 6/1997 |
| WO | 97/44339 | 11/1997 |
| WO | WO 97/44339 A1 | 11/1997 |
| WO | WO 98/55116 A1 | 12/1998 |
| WO | WO 98/55119 A1 | 12/1998 |
| WO | WO 98/55123 A1 | 12/1998 |
| WO | WO 98/55470 A1 | 12/1998 |
| WO | WO 98/55479 A1 | 12/1998 |
| WO | WO 99/21553 A1 | 5/1999 |
| WO | WO 99/21557 A1 | 5/1999 |
| WO | WO 99/41251 A1 | 8/1999 |
| WO | WO 99/41252 A1 | 8/1999 |
| WO | WO 99/51231 A1 | 10/1999 |
| WO | WO 99/51232 A1 | 10/1999 |
| WO | WO 99/51233 A1 | 10/1999 |
| WO | WO 99/51234 A1 | 10/1999 |
| WO | WO 99/51595 A1 | 10/1999 |
| WO | WO 99/51596 A1 | 10/1999 |
| WO | 00/04013 | 1/2000 |
| WO | WO 00/04013 A1 | 1/2000 |
| WO | WO 00/53178 A1 | 8/2000 |
| WO | WO 00/53179 A1 | 8/2000 |
| WO | WO 00/53180 A1 | 8/2000 |
| WO | WO 00/53181 A1 | 8/2000 |
| WO | WO 00/53185 A1 | 8/2000 |
| WO | WO 00/53602 A1 | 8/2000 |
| WO | WO 00/69433 A1 | 11/2000 |
| WO | WO 02/66459 A1 | 8/2002 |
| WO | WO 02/92565 A2 | 11/2002 |

OTHER PUBLICATIONS

Golub et al., Science, vol. 286, Oct. 15, 1999, pp. 531-537.*
Ashton et al 'Substituted Indole-5-carboxamides and -acetamides as Potent Nonpeptide GnRH Receptor Antagonist.' Bioorganic & Medicinal Chemistry Letters, 2001, vol. 11, pp. 1723-1726.
Ashton et al 'Potent Nonpeptide GnHR Receptor Antagonists Derived from Substituted Indole-5-carboxamides and -acetamides Bearing a Pyridine Side-Chain Terminus.' Bioorganic & Medicinal Chemistry Letters, 2001, vol. 11, pp. 1727-1731.
Ashton et al 'Orally Bioavailable, Indole-Based Nonpeptide GnHR Receptor Antagonists with High Potancy and Functional Activity.' Bioorganic and medicinal Chemistry Letters, 2001, vol. 11, pp. 2597-2602.
Chu et al 'Initial Structure-Activity Relationship of a Novel Class of Nonpeptidyl GnHR Receptor Antagonists: 2-Arylindoles.' Bioorganic and Medicinal Chemistry Letters, 2001, vol. 11, pp. 509-513.
Chu et al 'SAR Studies of novel 5-Substituted 2-Arylindoles as Nonpeptidyl GnHR Receptor Antagonists.' Bioorganic and Medicinal Chemistry Letters, 2001, vol. 11, pp. 515-517.
Freidinger, R, M. 'Nonpeptide ligands for peptide and protein receptors.' Current Opinion in Chemical Biology, 1999, vol. 3, pp. 395-406.
Goulet, M, T. 'Gonadotropin Releasing Hormone Antagonists.' Annual Reports in Medicinal Chemistry, 1995, vol. 30, pp. 169-178.

(Continued)

*Primary Examiner*—Laura L. Stockton

(57) ABSTRACT

The invention relates to a group of novel thieno-pyrrole compounds of Formula (I):

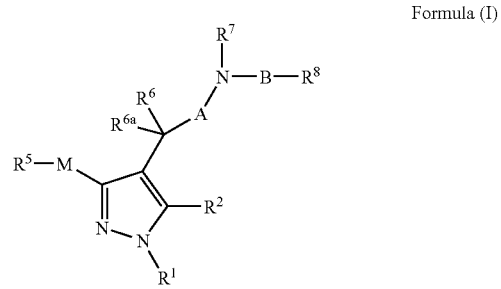

Formula (I)

wherein: $R^1$, $R^2$, $R^5$, $R^6$, $R^{6a}$, $R^7$, $R^8$, A, B and M are as defined in the specification, which are useful as gonadotrophin releasing hormone antagonists. The invention also relates to pharmaceutical formulations of said compounds, methods of treatment using said compounds and to processes for the preparation of said compounds.

12 Claims, No Drawings

OTHER PUBLICATIONS

Lin, et al '2-(3,5-Dimethylphenyl)tryptamine Derivatives That Bind to the GnHR Receptor.' Bioorganic & Medicinal Chemistry Letters, 2001, vol. 11, pp. 1073-1076.

Lin et al 'Heterocyclic Derivatives of 2-(3,5-Dimethylphenyl)tryptamine as GnHR Receptor Antagonists.' Bioorganic & Medicinal Chemistry Letters, 2001, vol. 11, pp. 1077-1080.

Simoene, J, P. 'Synthesis of chiral β-methyl tryptamine-derived GnHR antagonists.' Tetrahedron Letters, 2001, vol. 42, pp. 6459-6461.

Walsh et al 'A convergent synthesis of (S)-β-methyl-2-aryltryptamine based gonadotropin releasing hormone antagonists.' Tetrahedron, 2001, vol. 57, pp. 5233-5241.

Young et al '2-Arylindoles as Gonadotropin Releasing Hormone (GnHR) Antagonists: Optimization of the Tryptamine Side Chain.' Bioorganic & Medicinal Chemistry Letters, 2002, vol. 12, pp. 827-832.

Ujjainwalla, F 'Total synthesis of 6- and 7-azaindole derived GnHR antagonists.' Tetrahedron Letters, 2001, vol. 42, pp. 6441-6445.

Simeone et al 'Modification of the Pyridine Moiety of Non-peptidyl Indole GnHR Receptor Antagonists.' Bioorganic & Medicinal Chemistry Letters, 2002, vol. 12, pp. 3329-3332.

Gibbs, J, B 'Pharmaceutical Research in Molecular Oncology.' Cell, 1994, vol. 792, pp. 193-198.

* cited by examiner

PYRAZOLE DERIVATIVES AS GNRH INHIBITORS

CROSS-REFERENCE TO RELATED APPLICATIONS

This application is a US National Stage under 35 U.S.C § 371 of International Application No. PCT/GB2003/003623, filed Aug. 19, 2003, which claims priority under 35 U.S.C. § 119(a)–(d) to European Patent Application No. 02292075.5 filed on Aug. 21, 2002, the specification of which is incorporated by reference herein.

The present invention relates to compounds which are antagonists of gonadotropin releasing hormone (GnRH) activity. The invention also relates to pharmaceutical formulations, the use of a compound of the present invention in the manufacture of a medicament, a method of therapeutic treatment using such a compound and processes for producing the compounds.

Gonadotropin releasing hormone (GnRH) is a decapeptide that is secreted by the hypothalamus into the hypophyseal portal circulation in response to neural and/or chemical stimuli, causing the biosynthesis and release of luteinizing hormone (LH) and follicle-stimulating hormone (FSH) by the pituitary. GnRH is also known by other names, including gonadoliberin, LH releasing hormone (LHRH), FSH releasing hormone (FSH RH) and LH/FSH releasing factor (LH/FSH RF).

GnRH plays an important role in regulating the action of LH and FSH (by regulation of their levels), and thus has a role in regulating the levels of gonadal steroids in both sexes, including the sex hormones progesterone, oestrogens and androgens. More discussion of GnRH can be found in WO 98/5519 and WO 97/14697, the disclosures of which are incorporated herein by reference.

It is believed that several diseases would benefit from the regulation of GnRH activity, in particular by antagonising such activity. These include sex hormone related conditions such as sex hormone dependent cancer, benign prostatic hypertrophy and myoma of the uterus. Examples of sex hormone dependent cancers are prostatic cancer, uterine cancer, breast cancer and pituitary gonadotrophe adenoma.

The following disclose compounds purported to act as GnRH antagonists: WO 97/21435, WO 97/21703, WO 97/21704, WO 97/21707, WO 55116, WO 98/55119, WO 98/55123, WO 98/55470, WO 98/55479, WO 99/21553, WO 99/21557, WO 99/41251, WO 99/41252, WO 00/04013, WO 00/69433, WO 99/51231, WO 99/51232, WO 99/51233, WO 99/51234, WO 99/51595, WO 99/51596, WO 00/53178, WO 00/53180, WO 00/53179, WO 00/53181, WO 00/53185, WO 00/53602, WO 02/066477, WO 02/066478, WO 02/06645 and WO 02/092565.

It would be desirable to provide further compounds, such compounds being GnRH antagonists. Thus, according to the first aspect of the invention there is provided a compound of Formula (I),

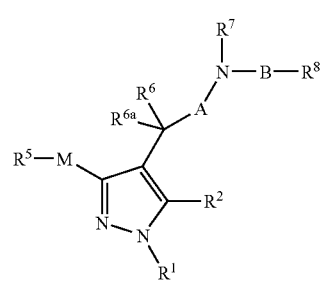

Formula (I)

wherein
A represents a direct bond or optionally substituted $C_{1-5}$alkylene;
B is a group of Formula (II):

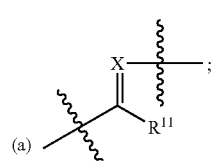

Formula (II)

wherein at position (a) Formula (II) is attached to the nitrogen atom and the group X is attached to $R^8$;
M is —$(CH_2)_{0-2}$—O—;
$R^1$ represents hydrogen; optionally substituted $C_{1-8}$alkyl; or $(CH_2)_b$—$R^a$, wherein
  $R^a$ represents $C_{3-8}$cycloalkyl and b is zero or an integer from 1 to 6;
$R^2$ represents an optionally substituted mono- or bi-cyclic aromatic ring structure wherein the optional substituents are selected from cyano, $NR^3R^{3a}$, optionally substituted $C_{1-8}$alkyl, optionally substituted $C_{1-8}$alkoxy or halo;
$R^3$ and $R^{3a}$ are independently selected from hydrogen; optionally substituted $C_{1-8}$alkyl and optionally substituted aryl;
$R^5$ is selected from an optionally substituted 3 to 8 membered heterocyclic ring containing from 1 to 4 heteroatoms independently selected from O, N and S; or a group of formula III-a; III-b; III-c; III-d; III-e; III-f, III-g, III-h, III-i or III-j:

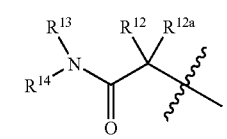

III-a

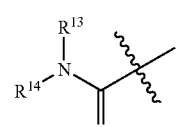

III-b

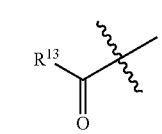

III-c

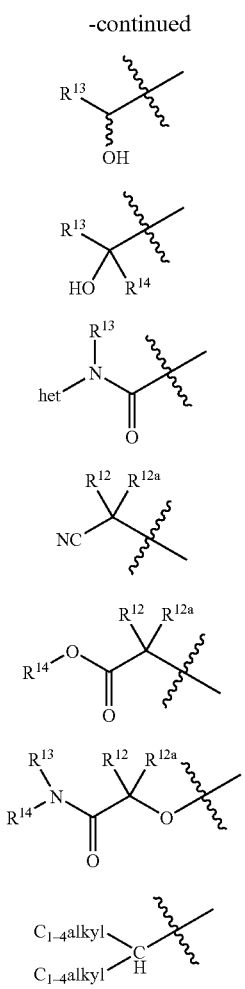

wherein het represents an optionally substituted 3 to 8 membered heterocyclic ring containing from 1 to 4 heteroatoms independently selected from O, N and S;

$R^6$ and $R^{6a}$, are independently selected from hydrogen and optionally substituted $C_{1-8}$alkyl; or $R^6$ and $R^{6a}$ together represent carbonyl;

$R^7$ represents hydrogen or optionally substituted $C_{1-8}$alkyl; or

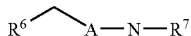

together from an optionally substituted 3- to 8-membered heterocyclic ring containing from 1 to 3 further heteroatoms independently selected from O, N and S, and $R^{6a}$ represents hydrogen or optionally substituted $C_{1-8}$alkyl;

X and $R^8$ are selected from:
  (i) X represents N and $R^8$ is selected from: cyano, hydrogen, hydroxy, —O—$R^b$, —N$R^b R^c$—C(O)O$R^b$, —CON$R^b R^c$ or NH—C(O)—$R^b$, where $R^b$ and $R^c$ are independently selected from hydrogen and $C_{1-4}$alkyl optionally substituted with hydroxy, amino, N—$C_{1-4}$alkylamino, N,N-di-$C_{1-4}$alkylamino, HO—$C_{2-4}$alkyl-NH— or HO—$C_{2-4}$alkyl-N($C_{1-4}$alkyl)-;
  (ii) X represents CH and $R^8$ represents $NO_2$; and
  (iii) X—$R^8$ represents O;

$R^{11}$ is a group of the formula: $N(R^9 R^{10})$ wherein $R^9$ represents hydrogen, aryl, an optionally substituted 3- to 10 membered heterocyclic ring or optionally-substituted $C_{1-8}$alkyl and $R^{10}$ represents hydrogen or optionally substituted $C_{1-8}$alkyl; or the structure $N(R^9 R^{10})$ represents an optionally-substituted 3- to 10 membered heterocyclic ring optionally containing from 1 to 3 further heteroatoms independently selected from O, N and S;

$R^{12}$ and $R^{12a}$ are independently selected from hydrogen or optionally substituted $C_{1-8}$alkyl; or $R^{12}$ and $R^{12a}$ together with the carbon to which they are attached form an optionally substituted 3 to 7-membered cycloalkyl ring;

$R^{13}$ and $R^{14}$ are selected from:
  (i) $R^{13}$ is selected from hydrogen; optionally substituted $C_{1-8}$alkyl; optionally substituted aryl; —$R^d$—Ar, where $R^d$ represents $C_{1-8}$alkylene and Ar represents optionally substituted aryl; and optionally substituted 3 to 8 membered heterocyclic ring optionally containing from 1 to 3 further heteroatoms independently selected from O, N and S; and $R^{14}$ is selected from hydrogen; optionally substituted $C_{1-8}$alkyl and optionally substituted aryl;
  (ii) where $R^5$ represents a group of formula III-a, III-b or III-i, then the group $NR^{13}(-R^{14})$ represents an optionally substituted 3 to 8 membered heterocyclic ring optionally containing from 1 to 3 further heteroatoms independently selected from O, N and S; or
  (iii) where $R^5$ represents structure III-e, then the group

represents an optionally substituted 3 to 8 membered heterocyclic ring optionally containing from 1 to 4 heteroatoms independently selected from O, N and S;

or a salt, pro-drug or solvate thereof.

According to a further feature of the first aspect of the invention there is provided a pharmaceutical formulation comprising a compound of Formula (1), or salt, pro-drug or solvate thereof, and a pharmaceutically acceptable diluent or carrier.

According to a further feature of the first aspect of the invention there is provided the following uses of a compound of Formula (I), or salt, pro-drug or solvate thereof:
(a) the use in the manufacture of a medicament for antagonising gonadotropin releasing hormone activity;
(b) the use in the manufacture of a medicament for administration to a patient, for reducing the secretion of luteinizing hormone by the pituitary gland of the patient; and
(c) the use in the manufacture of a medicament for administration to a patient, for therapeutically treating and/or preventing a sex hormone related condition in the patient, preferably a sex hormone related condition selected from prostate cancer and pre-menopausal breast cancer.

According to a further aspect of the invention there is provided a method of antagonising gonadotropin releasing hormone activity in a patient, comprising administering a compound of Formula (I), or salt, pro-drug or solvate thereof, to a patient.

Whilst pharmaceutically-acceptable salts of compounds of the invention are preferred, other non-pharmaceutically-acceptable salts of compounds of the invention may also be useful, for example in the preparation of pharmaceutically-acceptable salts of compounds of the invention.

Whilst the invention comprises compounds of the invention, and salts, pro-drugs or solvates thereof, in a further embodiment of the invention, the invention comprises compounds of the invention and salts thereof.

In the present specification, unless otherwise indicated, an alkyl, alkylene or alkenyl moiety may be linear or branched.

The term "alkylene" refers to the group —CH$_2$—. Thus, C$_8$ alkylene for example is —(CH$_2$)$_8$—.

The term "aryl" refers to phenyl or naphthyl.

The term "carbamoyl" refers to the group —CONH$_2$.

The term "halo" refers to fluoro, chloro, bromo or iodo.

The term "heterocyclyl" or "heterocyclic ring" refers to a 5–10 membered aromatic mono or bicyclic ring or a 5–10 membered saturated or partially saturated mono or bicyclic ring, said aromatic, saturated or partially unsaturated rings containing up to 5 heteroatoms independently selected from nitrogen, oxygen or sulphur, linked via ring carbon atoms or ring nitrogen atoms where a bond from a nitrogen is allowed, for example no bond is possible to the nitrogen of a pyridine ring, but a bond is possible through the 1-nitrogen of a pyrazole ring. Examples of 5- or 6-membered aromatic heterocyclic rings include pyrrolyl, furanyl, imidazolyl, triazolyl, pyrazinyl, pyrimidinyl, pyridazinyl, pyridinyl, isoxazolyl, oxazolyl, 1,2,4 oxadiazolyl, isothiazolyl, thiazolyl and thienyl. A 9 or 10 membered bicyclic aromatic heterocyclic ring is an aromatic bicyclic ring system comprising a 6-membered ring fused to either a 5 membered ring or another 6 membered ring. Examples of 5/6 and 6/6 bicyclic ring systems include benzofuranyl, benzimidazolyl, benzthiophenyl, benzthiazolyl, benzisothiazolyl, benzoxazolyl, benzisoxazolyl, indolyl, pyridoimidazolyl, pyrimidoimidazolyl, quinolinyl, isoquinolinyl, quinoxalinyl, quinazolinyl, phthalazinyl, cinnolinyl and naphthyridinyl. Examples of saturated or partially saturated heterocyclic rings include pyrrolinyl, pyrrolidinyl, morpholinyl, piperidinyl, piperazinyl, dihydropyridinyl and dihydropyrimidinyl. This definition further comprises sulphur-containing rings wherein the sulphur atom has been oxidised to an S(O) or S(O$_2$) group.

The term "aromatic ring" refers to a 5–10 membered aromatic mono or bicyclic ring optionally containing up to 5 heteroatoms independently selected from nitrogen, oxygen or sulphur. Examples of such "aromatic rings" include: phenyl, pyrrolyl, furanyl, imidazolyl, triazolyl, pyrazinyl, pyrimidinyl, pyridazinyl, pyridinyl, isoxazolyl, oxazolyl, 1,2,4 oxadiazolyl, isothiazolyl, thiazolyl and thienyl. Preferred aromatic rings include 'phenyl, thienyl and pyridyl.

The symbol

denotes where the respective group is linked to the remainder of the molecule.

For the avoidance of doubt, when

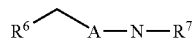

together form an optionally substituted 3- to 8-membered heterocyclic ring containing from 1 to 3 further heteroatoms independently selected from O, N and S, then the groups shown cyclise to form a nitrogen-containing heterocyclic ring, i.e

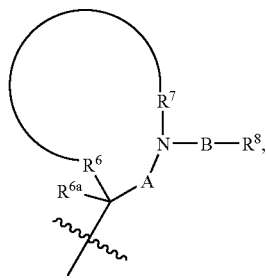

optionally containing from 1 to 3 further heteroatoms independently selected from O, N and S.

Examples of C$_{1-8}$alkyl include: methyl, ethyl, propyl, isopropyl, butyl, iso-butyl, tert-butyl and 2-methyl-pentyl; example of C$_{1-8}$alkylene include: methylene, ethylene and 2-methyl-propylene; examples of C$_{1-8}$alkoxy include methoxy, ethoxy and butyloxy; examples of N—C$_{1-4}$alkylamino include N-methylamino and N-ethylamino; examples of N,N-di-C$_{1-4}$alkylamino, examples of HO—C$_{2-4}$alkyl-NH include hydroxymethylamino hydroxyethylamino and hydroxypropyamino, examples of HO—C$_{2-4}$alkyl-N(C$_{1-4}$alkyl) include N-methyl-hydroxymethylamino, N-ethyl-hydroxyethylamino, and N-propyl-hydroxypropyamino.

It is to be understood that, insofar as certain of the compounds of the invention may exist in optically active or racemic forms by virtue of one or more asymmetric carbon atoms, the invention includes in its definition any such optically active or racemic form which possesses the property of antagonizing gonadotropin releasing hormone (GnRH) activity. The synthesis of optically active forms may be carried out by standard techniques of organic chemistry well known in the art, for example by synthesis from optically active starting materials or by resolution of a racemic form. Similarly, activity of these compounds may be evaluated using the standard laboratory techniques referred to hereinafter.

The invention also relates to any and all tautomeric forms of the compounds of the different features of the invention that possess the property of antagonizing gonadotropin releasing hormone (GnRH) activity.

It will also be understood that certain compounds of the present invention may exist in solvated, for example hydrated, as well as unsolvated forms. It is to be understood that the present invention encompasses all such solvated forms which possess the property of antagonizing gonadotropin releasing hormone (GnRH) activity.

Preferred compounds of Formula (1) are those wherein any one of the following or a combination of the following apply.

Preferably A represents optionally substituted C$_{1-5}$alkylene. Further preferably C$_{1-4}$alkylene. Most preferably methylene or ethylene.

Preferably M is —CH$_2$—O—.

Preferably R$^1$ represents hydrogen or optionally substituted C$_{1-6}$alkyl. More preferably R$^1$ represents hydrogen, methyl, ethyl or tert-butyl. Most preferably R$^1$ represents hydrogen.

Preferably R$^2$ represents an optionally substituted monocyclic aromatic ring structure wherein the optional substituents are selected from cyano, NR$^3$R$^{3a}$, optionally substituted C$_{1-8}$alkyl (preferably, C$_{1-4}$alkyl, eg, methyl or ethyl), optionally substituted C$_{1-8}$alkoxy (preferably, C$_{1-6}$alkoxy, eg, methoxy, ethoxy or tert-butoxy) or halo (eg, F, Br or Cl) wherein R$^3$ and R$^{3a}$ are independently selected from hydrogen, $C_{1-6}$alkyl or aryl. Further preferably $R^2$ is optionally substituted phenyl wherein the optional substituents are selected from cyano, $NR^3R^{3a}$, optionally substituted $C_{1-4}$alkyl, optionally substituted $C_{1-6}$alkoxy, F, Br or Cl wherein $R^3$ and $R^{3a}$ are as defined above. Yet further preferably $R^2$ is optionally substituted phenyl wherein the optional substituents are selected from methyl, ethyl, methoxy, ethoxy, tert-butoxy, F or Cl. Most preferably $R^2$ represents

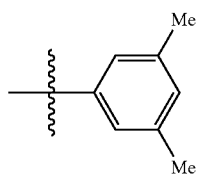

wherein Me represents methyl. Preferably $R^2$ bears 1, 2 or 3 substituents.

Preferably $R^3$ and $R^{3a}$ are independently selected from hydrogen; optionally substituted $C_{1-6}$alkyl and, optionally substituted aryl. Further preferably $R^3$ and $R^{3a}$ are independently selected from methyl, ethyl, tert-butyl and phenyl.

Preferably $R^5$ is selected from a group of formula III-a, III-g, III-h, or III-i or III-j:

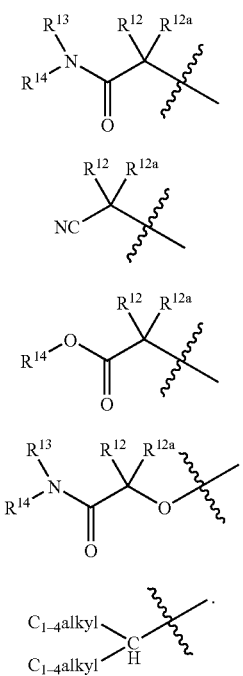

Further preferably $R^5$ is selected from one of the following groups:

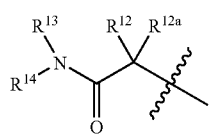

Yet further preferably $R^5$ is selected from one of the following groups:

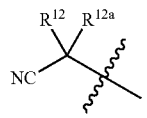
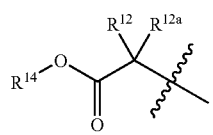

wherein Me represents methyl.

Most preferably $R^5$ is selected from one of the following groups:

In one embodiment, $R^6$ and $R^{6a}$ each represent hydrogen and A represents $C_{1-4}$alkylene (preferably methylene).

In a further embodiment of the invention $R^6$ represents hydrogen, $R^{6a}$ represents methyl, and A represents $C_{1-4}$alkylene (preferably methylene).

Preferably $R^7$ is selected from hydrogen or optionally-substituted $C_{1-6}$alkyl. Further preferably $R^7$ represents hydrogen, methyl, ethyl or tert-butyl.

Preferably X and $R^8$ represent either:—
(a) X represents N and $R^8$ represents cyano or —C(O)O—$R^b$; or
(b) X represents N and $R^8$ represents hydrogen.

Further preferably X represents N and $R^8$ represents cyano or —C(O)O—$R^b$; wherein $R^b$ represents $C_{1-6}$alkyl;

In a further embodiment of the invention X represents N and $R^8$ represents —$CONR^bR^c$ wherein $R^b$ and $R^c$ are as defined above.

Preferably $R^9$ comprise part of the group $N(R^9R^{10})$ or is hydrogen, optionally substituted aryl, an optionally substituted 3- to 10 membered heterocyclic ring or optionally substituted $C_{1-4}$alkyl wherein the optional substituents are selected from: hydroxy, amino, nitro, cyano, optionally-substituted aryl, optionally substituted 3- to 8-membered heterocyclyl containing from 1 to 4 heteroatoms independently selected from O, N and S, —O—$R^b$, $C(O)NR^bR^c$, —$NR_bR^c$, —$NR^cC(O)$—$R^b$, —$C(O)NR^bR^c$, —$NR^cS(O_{0-2})R^b$ and —$S(O_{0-2})R^b$, wherein $R^b$ and $R^c$ are as defined above.

When $R^9$ is a $C_{1-6}$alkyl group substituted by an optionally-substituted 3 to 10 membered heterocyclic ring containing from 1 to 4 heteroatoms independently selected from O, N and S, the heterocyclic ring is preferably selected from pyridyl, thienyl, piperidinyl, imidazolyl, triazolyl, thiazolyl, pyrrolidinyl, piperazinyl, morpholinyl, imidazolinyl, benztriazolyl, benzimidazolyl, pyrimidinyl, pyrazinyl, pyridazinyl, oxazolyl, furanyl, pyrrolyl, 1,3-dioxolanyl, 2-azetinyl, each of which is optionally substituted. Further preferably a group of formula VI-a, VI-b, VI-c, VI-d, VI-e, VI-f, VI-g, VI-h, VI-i, VI-j or VI-k:, wherein each group is optionally substituted by one or more groups selected from $R^{16}$.

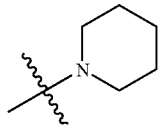

VI-a

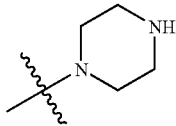

VI-b

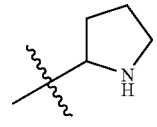

VI-c

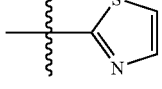

VI-d

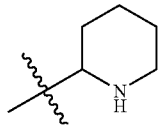

VI-e

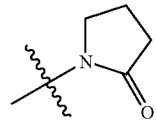

VI-f

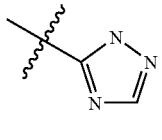

VI-g

-continued

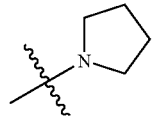

VI-h

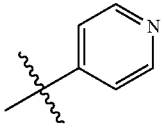

VI-i

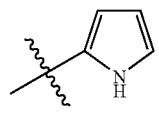

VI-j

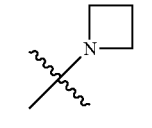

VI-k

Most preferably a group of formula VI-b, VI-i or VI-j:

VI-b

VI-i

VI-j wherein
$R^{16}$ represents hydrogen, aryl, a 3- to 10 membered heterocyclic ring or optionally substituted $C_{1-4}$alkyl wherein the optional substituents are selected from: hydroxy, amino, nitro, cyano, optionally-substituted phenyl, optionally substituted 3- to 8-membered heterocyclyl containing from 1 to 4 heteroatoms independently selected from O, N and S, —O—$R^b$, $C(O)NR^bR^c$, —$NR^bR^c$, —$NR^cC(O)$—$R^b$, —$C(O)NR^bR^c$, —$NR^cS(O_{0-2})R^b$ and —$S(O_{0-2})R^b$, wherein $R^b$ and $R^c$ are as defined above;

Preferably $R^{10}$ comprises part of the group $N(R^9R^{10})$ or is optionally substituted $C_{1-6}$alkyl. Further preferably $R^{10}$ comprises part of the group $N(R^9R^{10})$ or is selected from: methyl, ethyl or tert-butyl.

When $N(R^9R^{10})$ represent an optionally substituted 3- to 10-membered heterocyclic ring, $N(R^9R^{10})$ is preferably selected from a 5- or 6-membered monocyclic ring containing between 1 and 3 (preferably 1 or 2) heteroatoms independently selected from O, N and S. Further preferably a 5- or 6-membered monocyclic ring containing between 1 and 3 (preferably 1 or 2) heteroatoms independently selected from O, N and S, selected from pyrrolidinyl, thienyl, pyrazolidinyl, piperidinyl, morpholinyl, thiomorpholinyl piperazinyl, imidazole, azetidinyl or azetinyl. Further preferably the structure $N(R^9R^{10})$ is a heterocyclic ring selected from an optionally-substituted group of formula, IV-a, IV-b, IV-c, IV-d and IV-e, wherein the optional substituents are preferably selected from the groups listed for $R^{15}$ below

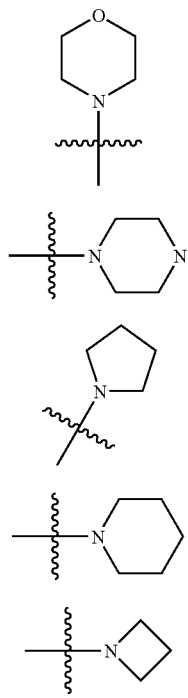

IV-a

IV-b

IV-c

IV-d

IV-e

Further preferably the structure $N(R^9R^{10})$ is selected from a group of formula Va, Vb or Vc:

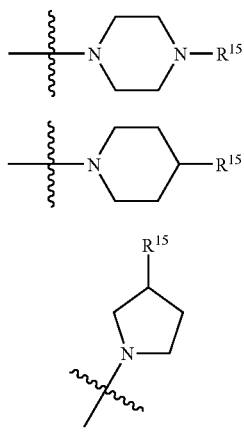

V-a

V-b

V-c

Most preferably the structure $N(R^9R^{10})$ is a group of formula V-c: $R^{15}$ represents hydrogen, optionally substituted aryl, an optionally substituted 3- to 10 membered heterocyclic ring or optionally substituted $C_{1-4}$alkyl wherein the optional substituents on aryl, a heterocyclic ring or $C_{1-4}$alkyl are selected from: hydroxy, amino, nitro, cyano, halo, optionally-substituted aryl, optionally substituted 3- to 8-membered heterocyclyl containing from 1 to 4 heteroatoms independently selected from O, N and S, $—O—R^b$, $C(O)NR^bR^c$, $—NR^bR^c$, $—NR^cC(O)—R^b$, $—C(O)NR^bR^c$, $—NR^cS(O_{0-2})R^b$ and $—S(O_{0-2})R^b$, wherein $R^b$ and $R^c$ are as defined above. Preferably $R^{15}$ is heterocyclyl. Further preferably $R^{15}$ is selected from: pyridyl, pyrazinyl, pyridazinyl, pyrimidinyl or thiazolyl. Most preferably $R^{15}$ is pyridyl.

In a further embodiment of the invention $N(R^9R^{10})$ represent an optionally substituted 3- to 10-membered heterocyclic ring, wherein the optional substituents are selected from $R^{15}$ as defined above.

Preferably $R^{12}$ and $R^{12a}$ are independently selected from: hydrogen, optionally substituted $C_{1-6}$alkyl or $R^{12}$ and $R^{12a}$ together with carbon to which they are attached from an optionally substituted 3- to 6-membered cycloalkyl ring. Further preferably $R^{12}$ and $R^{12a}$ are independently selected from: hydrogen, methyl, ethyl or tert-butyl. Most preferably $R^{12}$ and $R^{12a}$ are both methyl.

Preferably $R^{13}$ and $R^{14}$, are independently selected from hydrogen, optionally substituted $C_{1-6}$alkyl, optionally substituted phenyl and $—R^d$-phenyl, where $R^d$ represents $C_{1-6}$alkylene or and an optionally substituted 3- to 8-membered heterocyclic ring (preferably, a 5- or 6-membered monocyclic ring) containing from 1 to 3 (preferably 1 or 2) further heteroatoms independently selected from O, N and S. Further preferably $R^{13}$ and $R^{14}$, are independently selected from hydrogen or $C_{1-6}$alkyl.

Where optional substitution is mentioned at various places, this refers to one, two, three or more optional substituents. Unless otherwise indicated above (ie, where a list of optional substituents is provided), each substituent can be independently selected from $C_{1-8}$alkyl (eg, $C_2$ alkyl, and most preferably methyl, ethyl or tert-butyl); $C_{3-8}$cycloalkoxy, preferably cyclopropoxy, cyclobutoxy or cyclopentoxy; $C_{1-6}$alkoxy, preferably methoxy or $C_{2-4}$alkoxy; halo, preferably Cl or F; $Hal_3C—$, $Hal_2CH—$, $HalCH_2—$, $Hal_3CO—$, $Hal_2CHO$ or $Hal\,CH_2O$, wherein Hal represents halo (preferably F); $R^gCH_2O—$, $R^bC(O)N(R)—$, $R^hSO_2N(R)—$ or $R^g—R^hN—$, wherein $R^g$ and $R^h$ independently represent hydrogen or $C_{1-8}$alkyl (preferably methyl or $C_{2-6}$alkyl or $C_{2-4}$alkyl), or $R^g—R^hN—$ represents an optionally substituted $C_{3-8}$, preferably $C_{3-6}$, heterocyclic ring optionally containing from 1 to 3 further heteroatoms independently selected from O, N and S; hydrogen; or $R^kC(O)O—$ or $R^kC(O)—$, $R^k$ representing hydrogen, optionally substituted phenyl or $C_{1-6}$alkyl (preferably methyl, ethyl, iso-propyl or tert-butyl). For optional substitution of the heterocyclic ring represented by $R^g—R^hN—$, at least one (eg, one, two or three) substituents may be provided independently selected from $C_{1-6}$alkyl (eg, $C_{2-4}$alkyl, more preferably methyl); phenyl; $CF_3O—$; $F_2CHO—$; $C_{1-8}$alkoxy, preferably methoxy, ethoxy or $C_{3-6}$alkoxy; $C_{1-8}$alkoxyC(O), preferably methoxycarbonyl, ethoxycarbonyl, tert-butoxycarbonyl or $C_{3-6}$alkoxyC(O)—; phenoxycarbonyl; phenoxy; $C_{1-8}$alkanoyl, preferably acetyl, ethanoyl or $C_{3-6}$alkyanoyl; carboxy; $C_{1-8}$alkylS(O)$_{nn}$ wherein nn is an integer between 0 and 2, preferably methylthio, ethylthio, $C_{3-6}$alkylthio, methylsulphinyl, ethylsulphinyl, $C_{3-6}$alkylsulphinyl, methylsulphonyl, ethylsulphonyl or $C_{3-6}$alkylsulphonyl; hydroxy; halo (eg, F, Cl or Br); $R^mR^nN—$ where $R^m$ and $R^n$ are independently hydrogen or $C_{1-6}$alkyl (preferably $C_{2-4}$alkyl, more preferably methyl, most preferably $R^m=R^n=$methyl); and nitro.

Where optional substitution of a ring is mentioned at various places, this most preferably refers to one, two, three or more substituents selected from $C_{1-8}$alkyl (eg, $C_{2-6}$alkyl, and most preferably methyl); $C_{1-8}$alkoxy, preferably methoxy, ethoxy or $C_{3-6}$alkoxy; $C_{1-8}$alkylS(O)$_{nn}$ wherein nn is an integer between 0 and 2, preferably methylthio, ethylthio, $C_{3-6}$alkylthio, methylsulphinyl, ethylsulphinyl, $C_{3-6}$alkylsulphinyl, methylsulphonyl, ethylsulphonyl or $C_{3-6}$alkylsulphonyl; halo (eg, F, Cl or Br); cyano; and $NO_2$.

A preferred group of compounds of the invention comprise compounds of Formula (I) wherein:
$R^{11}$ is a group of the formula: $N(R^9R^{10})$; and
$N(R^9R^{10})$ represents an optionally-substituted 3- to 8-membered heterocyclic ring optionally containing from 1 to 3 further heteroatoms independently selected from O, N and S, preferably substituted by heterocyclyl;

or a salt, pro-drug or solvate thereof.

A preferred group of compounds of the invention comprise compounds of Formula (I) wherein:
$R^{11}$ is a group of the formula: $N(R^9R^{10})$;
$R^9$ is a $C_{1-6}$alkyl group substituted by an optionally-substituted 3 to 8 membered heterocyclic ring containing from 1 to 4 heteroatoms independently selected from O, N and S; and
$R^{10}$ represents hydrogen or $C_{1-6}$alkyl or a salt, pro-drug or solvate thereof.

A preferred group of compounds of the invention comprises a compound of Formula (Ia):

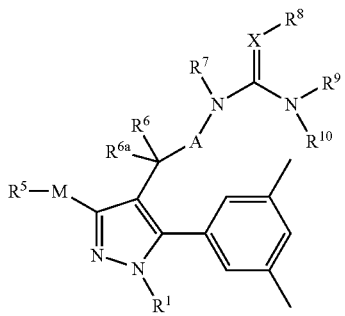

Formula (Ia)

wherein:
A, B, M, X, $R^1$, $R^5$, $R^6$, $R^{6a}$, $R^7$, $R^8$, $R^9$, $R^{10}$, $R^{11}$, $R^{12}$ and $R^{12a}$ are as defined above; or a salt, pro-drug or solvate thereof.

A preferred group of compounds of the invention comprises a compound of Formula (Ib):

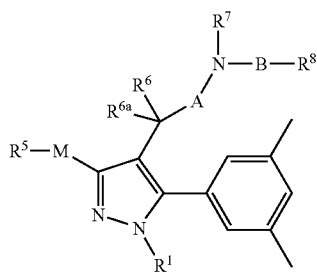

Formula (Ib)

wherein:
$R^5$ is selected from: IIIa, IIIb, IIIg, IIIi or IIIj:

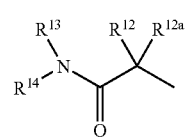

III-a

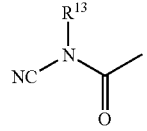

III-b

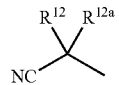

III-g

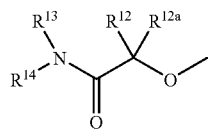

III-i

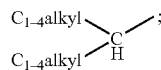

III-j and A, B, M, X, $R^1$, $R^5$, $R^6$, $R^{6a}$, $R^7$, $R^8$, $R^9$, $R^{10}$, $R^{11}$, $R^{12}$, $R^{12a}$, $R^{13}$, and $R^{14}$ are as defined above;

or a salt, pro-drug or solvate thereof.

A further preferred group of compounds of the invention comprises a compound of Formula (Ic):

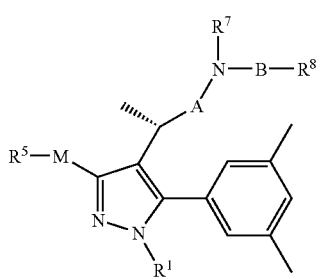

Formula (Ic)

wherein:
$R^5$ is selected from a IIIa, IIIb, IIIg, IIIi or IIIj:

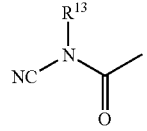

III-a

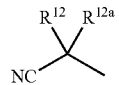

III-b

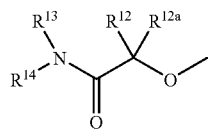

III-g

-continued

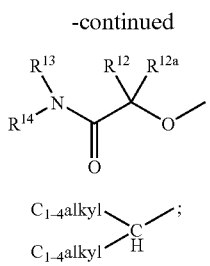

and A, B, M, X, $R^1$, $R^6$, $R^{6a}$, $R^7$, $R^8$, $R^9$, $R^{10}$, $R^{11}$, $R^{12}$, $R^{12a}$, $R^{13}$, and $R^{14}$ are as defined above;

or a salt, pro-drug or solvate thereof.

A yet further preferred group of compounds of the invention comprises a compound of Formula (Ia), (Ib) or (Ic) wherein:

$R^5$ is a group of formula IIIa:

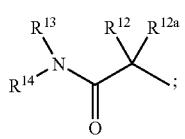

$NR^{13}(-R^{14})$ represents an optionally substituted 7- to 8-membered bicyclic heterocyclic ring and A, B, X, $R^1$, M, $R^6$, $R^{6a}$, $R^7$, $R^8$, $R^9$, $R^{10}$, $R^{11}$, $R^{12}$ and $R^{12a}$ are as defined above;

or a salt, pro-drug or solvate thereof.

A preferred compound according to the present invention is:

3-[2,2-dimethyl-3-oxo-3-(7-azabicyclo[2.2.1]heptan-7-yl) propyl]-4-[(1Z)-({2-[3-(2,2-dimethyl-3-oxo-3-pyrrolidin-1-yl)pyrrolidin-1-yl)methyl]aminoethyl]-5-(3,5-dimethylphenyl)-1H-pyrazole;

or a salt, pro-drug or solvate thereof.

In a further embodiment particularly preferred compounds according to the present invention are wherein the compound is selected from:

isopropyl (1Z)-({2-[3-(2,2-dimethyl-3-oxo-3-pyrrolidin-1-ylpropoxy)-5-(3,5-dimethylphenyl)-1H-pyrazol-4-yl]ethyl}amino)(3-pyridin-4ylpyrrolidin-1-yl)methylidenecarbamate;

isopropyl (1Z)-({2-[3-(2,2-dimethyl-3-oxo-3-(7-azabicyclo[2.2.1]hept-7-yl)propoxy)-5-(3,5-dimethylphenyl)-1H-pyrazol-4-yl]ethyl}amino)(3-pyridin-4-ylpyrrolidin-1-yl)methylidenecarbamate;

isopropyl (1Z)-({2-[3-[3-(diethylamino)-2,2-dimethyl-3-oxopropoxy]-5-(3,5-dimethylphenyl)-1H-pyrazol-4-yl]ethyl}amino)(3-pyridin-4-ylpyrrolidin-1-yl)methylidenecarbamate;

N-{2-[3-[3-(diethylamino)-2,2-dimethyl-3-oxopropoxy]-5-(3,5-dimethylphenyl)-1H-pyrazol-4-yl]ethyl}-3-pyridin-4-ylpyrrolidine-1-carboxamide;

or a salt, pro-drug or solvate thereof.

According to a further feature of the first aspect of the invention there is provided a pharmaceutical formulation comprising a compound of Formula (Ia), Formula (Ib), Formula (Ic) or preferred compounds of the invention, or salt, pro-drug or solvate thereof, and a pharmaceutically acceptable diluent or carrier.

According to a further feature of the first aspect of the invention there is provided the following uses of a compound of Formula (Ia), Formula (Ib), Formula (Ic) or preferred compounds of the invention, or salt, pro-drug or solvate thereof:

(a) the use in the manufacture of a medicament for antagonising gonadotropin releasing hormone activity;

(b) the use in the manufacture of a medicament for administration to a patient, for reducing the secretion of luteinizing hormone by the pituitary gland of the patient; and (c) the use in the manufacture of a medicament for administration to a patient, for therapeutically treating and/or preventing a sex hormone related condition in the patient, preferably a sex hormone related condition selected from prostate cancer and pre-menopausal breast cancer.

The compounds of Formula (I) may be administered in the form of a pro-drug which is broken down in the human or animal body to give a compound of the Formula (I). Examples of pro-drugs include in-vivo hydrolysable esters of a compound of the Formula (I).

Various forms of pro-drugs are known in the art. For examples of such pro-drug derivatives, see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

An in-vivo hydrolysable ester of a compound of the Formula (I) containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters.

An in-vivo hydrolysable ester of a compound of the Formula (1) containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of Formula (I) can be prepared by a process comprising a step selected from (a) to (f) as follows, these processes are provided as a further feature of the invention:—

(a) for compounds wherein X is N and $R^8$ is CN, reaction of a compound of formula XXXII as follows

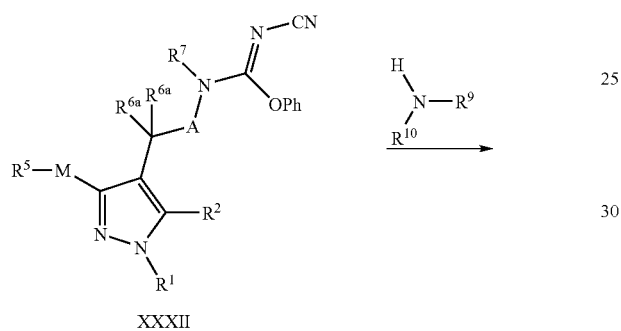

XXXII

XXXIII (b) for compounds wherein X is N and $R^8$ is hydrogen, cleavage of the cyano group of compound of formula XXXIII in the presence of acid to produce compound of formula XXXIV

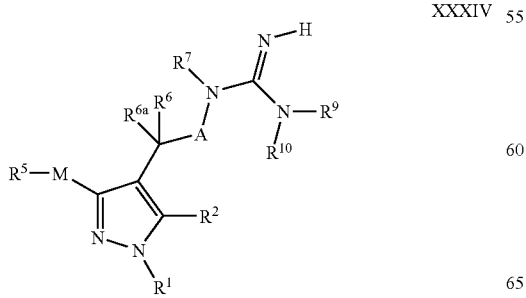

XXXIV (c) for compounds wherein X is CH and $R^8$ is $NO_2$, reaction of compound of formula XXXV as follows

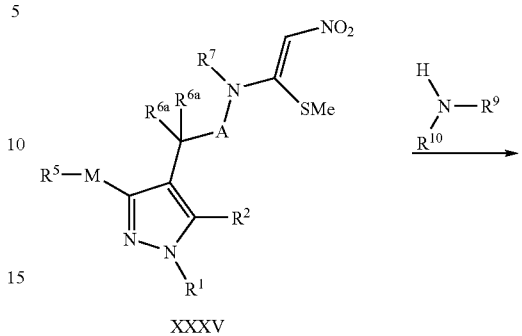

XXXV

XXXVI (d) for compounds where X—$R^8$ is O, reaction of compound of formula XXXVII as follows

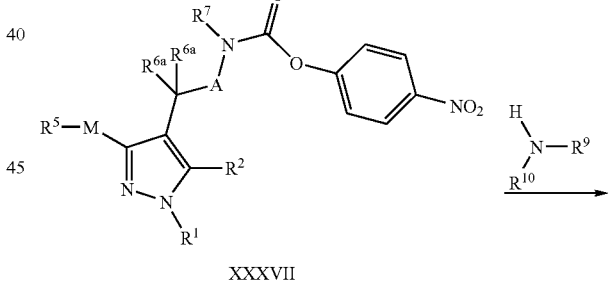

XXXVII

XXXVIII (e) for compounds where X—$R^8$ is O, reaction of compound of formula XXXIX as follows

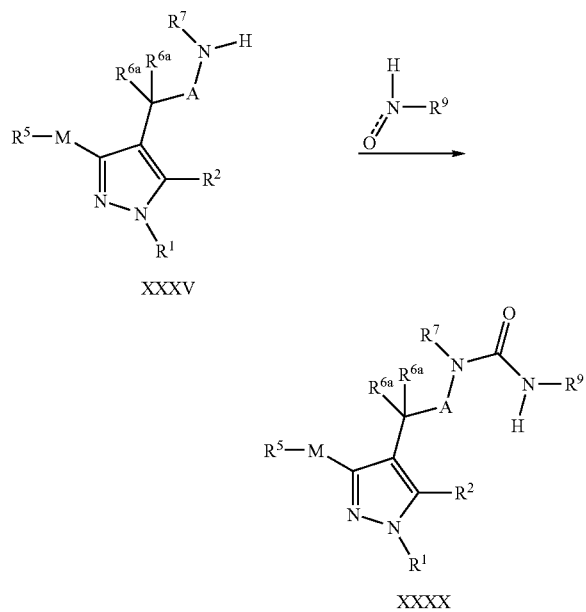

XXXV

XXXX (f) to form a compound wherein X is nitrogen and Reaction of a compound of formula XXXXI as follows

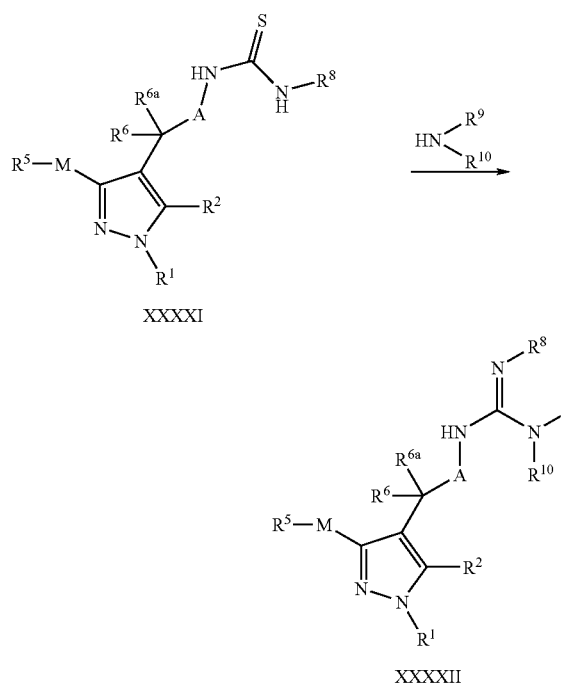

XXXXI

XXXXII and thereafter if necessary:
i) converting a compound of the Formula (I) into another compound of the Formula (I);
ii) removing any protecting groups;
iii) forming a salt, pro-drug or solvate.

It will be appreciated by those skilled in the art that in the processes of the present invention certain functional groups such as hydroxyl or amino groups in the starting reagents or intermediate compounds may need to be protected by protecting groups. Thus, the preparation of the compounds of Formula (I) may involve, at an appropriate stage, the addition and subsequent removal of one or more protecting groups.

The protection and de-protection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The de-protection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The de-protection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

EXPERIMENTAL

General Reaction Schemes

Scheme a

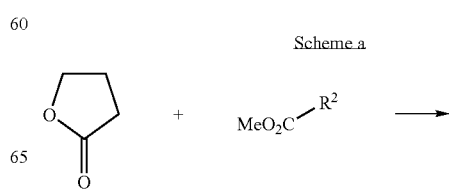

-continued

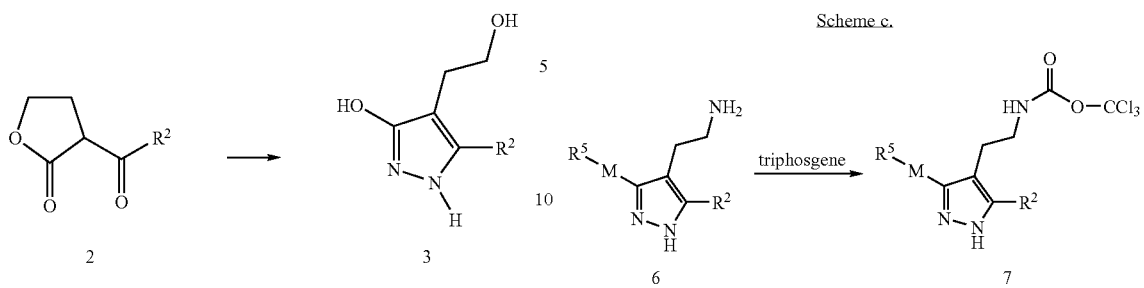

Pyrazoles, such as 3 can be synthesised in two steps (Scheme a):
(1) by the reaction of a lactone with the appropriate ester using a Claisen condensation to form a compound of formula 2, under conditions of an inert atmosphere, such as argon, at a temperature of about 0° C. in a suitable solvent such as THF.
(2) followed by cyclization of a compound of formula 2 with hydrazine to form the pyrazole 3, at a room temperature in a suitable solvent such as ethanol.

Scheme b

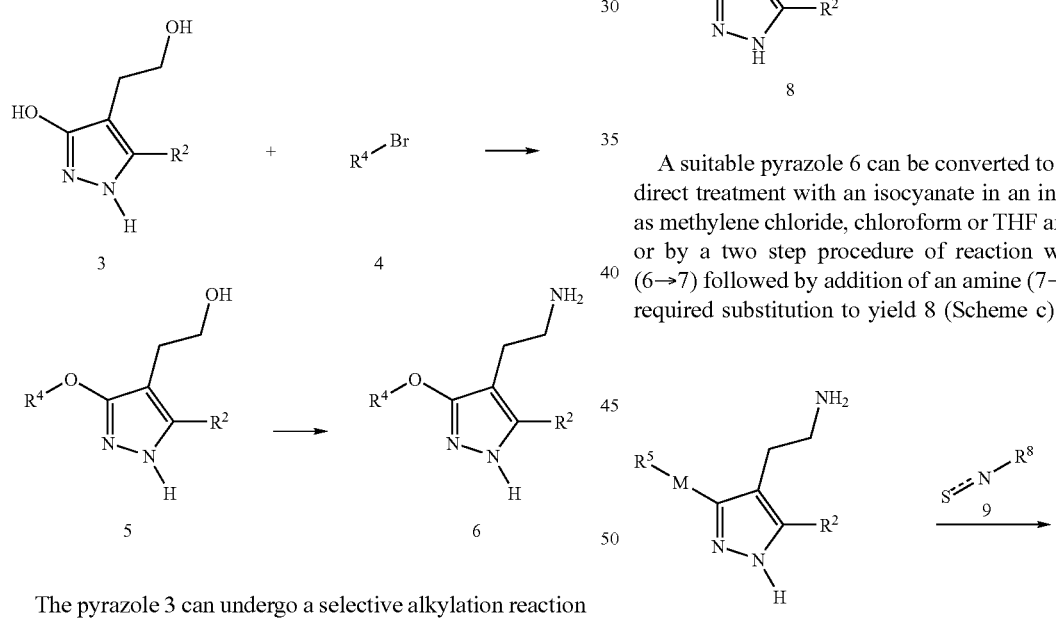

The pyrazole 3 can undergo a selective alkylation reaction with a compound of formula 4, under conditions of an inert atmosphere, such as argon, in the presence of a suitable base, such as potassium carbonate in the a suitable solvent such as DMA at a temperature of about 90° C., to form a compound of formula 5. Then the amine 6 can be prepared from a compound of formula 5 and phthalimide using a Mitsunobu reaction with an activating agent such as diethyldiazocarboxylate (DEAD), diisopropyldiazocarboxylate or the like with triphenylphosphine, tri-butylphosphine and the like, in an inert solvent such as benzene, toluene, tetrahydrofuran or mixtures thereof, followed by deprotection with hydrazine (Scheme b).

Scheme c.

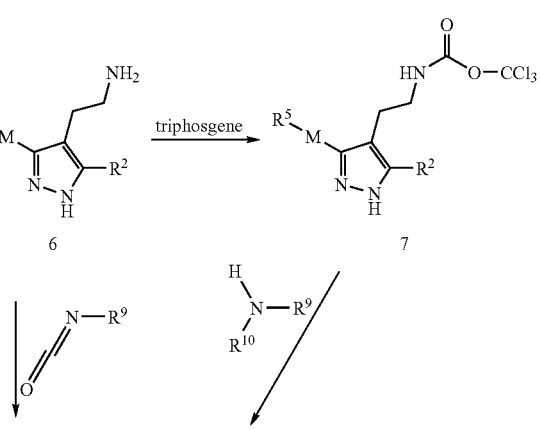

A suitable pyrazole 6 can be converted to a urea by either direct treatment with an isocyanate in an inert solvent such as methylene chloride, chloroform or THF and the such like, or by a two step procedure of reaction with triphosgene (6→7) followed by addition of an amine (7→8), bearing the required substitution to yield 8 (Scheme c).

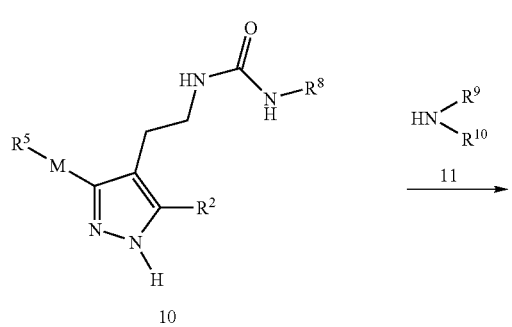

-continued

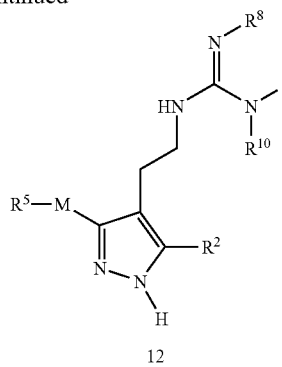

12

A suitable pyrazole (6) can be converted to a guandine or guanidine derivative (12) by reaction with a suitable isothiocyanate (9) to form a compound of formula 10, followed by displacement by a suitable amine (11) (Scheme d).

Thus, according to a further feature of the invention there is provided a process for the synthesis of a substituted pyrazole of formula XXXXV which comprises reaction of a compound of formula XXXXIII with hydrazine.

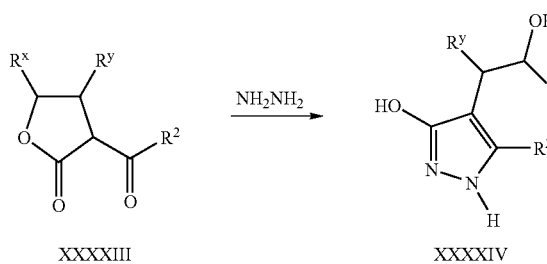

XXXXIII                    XXXXIV wherein:
$R^2$ is as defined above; and
$R^x$ and $R^y$ are independently selected from: optionally substituted alkyl, optionally substituted aryl or optionally substituted heteocyclyl.

According to a further feature of the invention there is provided an intermediate compound of formula XXXXIII as defined above.

EXAMPLES

The invention will now be illustrated with the following non-limiting Examples in which, unless otherwise stated:

(i) evaporations were carried out by rotary evaporation in vacuo and work-up procedures were carried out after removal of residual solids such as drying agents by filtration;

(ii) operations were carried out at room temperature, that is in the range 18–25° C. and under an atmosphere of an inert gas such as argon or nitrogen;

(iii) yields are given for illustration only and are not necessarily the maximum attainable;

(iv) the structures of the end-products of the Formula (1) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis;

(vi) chromatography was performed on silica (Merck Keiselgel: Art.9385);

| Abbreviations | |
|---|---|
| DCC | 1,3-dicyclohexylcarbodiimide |
| DEAD | diethylazodicarboxylate |
| DMSO | dimethyl sulphoxide |
| DMAP | 4-dimethylaminopyridine |
| DMF | dimethylformamide |
| DNS | 2,4-dinitrobenzenesulphonyl |
| EDC | 1-(3-dimethylaminopropyl)-3-ethylcarbodiimide hydrochloride |
| HOBt | 1-hydroxybenotriazole |
| LHMDS | lithium bis(trimethylsilyl)amide |
| THF | tetrahydrofuran |

Starting Materials

The starting material were prepared as follows:—

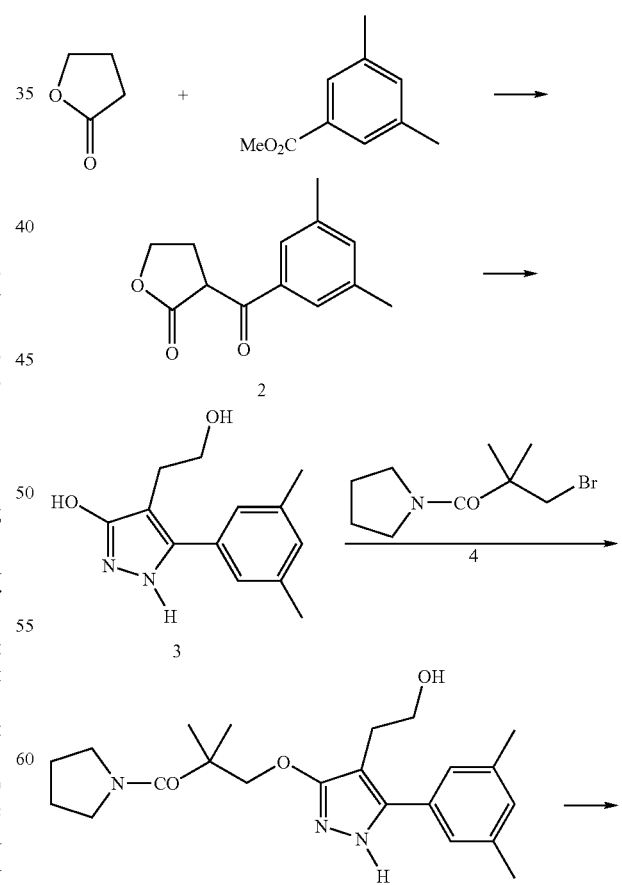

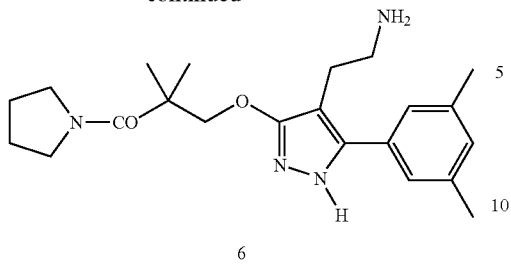

6

A solution of methyl 3,5-dimethylbenzoate (25 g; 152 mmol) and butyrolactone (40 ml; 520 mmol) in THF (300 ml) under argon was cooled to 0° C. and treated dropwise with LHMDS (200 ml; 200 mmol; 1M in hexanes). The mixture was stirred and allowed to warm to room temperature overnight. The THF was evaporated. The residue was taken up in $Et_2O$ and the organic phase was washed with sat. aq. $NaHCO_3$, brine and dried over $MgSO_4$. The residue was purified by flash chromatography eluting with increasingly polar mixtures of EtOAc/hexanes (20 to 40% EtOAc) to give an oil which slowly crystallised to give 2 as a white solid (9.2 g). During the chromatography, the starting material methyl 3,5-dimethylbenzoate (12.4g) was recovered.

Yield: 55% based on recovered methyl 3,5-dimethylbenzoate.

$^1$H NMR spectrum ($CDCl_3$): 2.39 (s, 6H); 2.5 (m, 1H); 2.82 (m, 1); 4.41 (m, 1H); 4.51 (m, 2H); 7.25 (s, 1H); 7.65 (s, 2H).

MS-ESI: 219 [M+H]$^+$

Compound 2 (7.43 g; 34 mmol) was dissolved in EtOH (200 ml) and hydrazine hydrate (17.2 ml; 354 mmol) was added. The mixture was stirred for 30 min. The solvent was evaporated and the residue was triturated with pentane to give 3 as a white solid (7.05 g).

Yield: 90%

$^1$H NMR spectrum (DMSO $d_6$): 2.32 (s, 6H); 2.58 (t, 2H); 3.50 (t, 2H); 4.8 (br s, 1H); 7.01 (s, 1H); 7.14 (s, 2H); 9.5 (br s, 1H).

MS-ESI: 233 [M+H]$^+$

A mixture of 3 (4.26 g; 18.4 mmol) and 4 (4.51 g; 19.3 mmol) in DMA (40 ml) under argon was treated with $K_2CO_3$ (5.07 g; 36.7 mmol). The mixture was stirred and heated at 90° C. for 2 h. The mixture was poured into sat. aq. $NaHCO_3$, extracted with EtOAc and the organic phase was washed with water, brine and dried over $MgSO_4$. The residue was purified by flash chromatography eluting with increasingly polar mixtures of EtOAc/$CH_2Cl_2$ (0 to 100% EtOAc) to give the alcohol 5 as a pale yellow oil (6.56 g).

Yield: 93%

$^1$H NMR spectrum (DMSO $d_6$): 1.30 (s, 6H); 1.8 (m, 4H); 2.33 (s, 6H); 2.55 (m, 2H); 3.32 (m, 2H); 3.5 (m, 4H); 4.17 (s, 2H); 4.62 (t, 1H); 7.04 (s, 1H); 7.16 (s, 2H); 11.9 (br s, 1H).

MS-ESI: 386 [M+H]$^+$

A mixture of 5 (3.85 g; 10 mmol), phthalimide (1.62 g; 11 mmol) and triphenylphosphine (10.5 g; 40 mmol) in TBF (100 ml) at 0° C. under argon was treated with DEAD (6.33 ml; 40 mmol). The mixture was stirred at this temperature for 1 h when water was added. The mixture was extracted with $Et_2O$ and the organic phase was washed with water, brine and dried over $MgSO_4$.

Evaporation gave a crude solid which, without further purification, was immediately taken up in EtOH (50 ml) and treated with hydrazine hydrate (5 ml; 100 mmol). The mixture was stirred for 1.5 h and then the EtOH was partially evaporated. Addition of $CH_2Cl_2$ caused precipitation of phthalhydrazide which was filtered and rinsed with $CH_2Cl_2$. The filtrate was evaporated and the residue was purified by flash chromatography eluting with increasingly polar mixtures of EtOAc/$CH_2Cl_2$ (0 to 100% EtOAc) and then MeOH/ $CH_2Cl_2$ (0 to 8% MeOH) to give 6 as a beige solid (2.34 g).

Yield: 61%

$^1$H NMR spectrum (DMSO $d_6$):1.30 (s, 6H); 1.79 (m, 4H); 2.33 (s, 6H); 2.52 (m, 2H); 2.67 (t, 2H); 3.5 (m, 4H); 4.18 (s, 2H); 7.03 (s, 1H); 7.14 (s, 2H); 8.95 (br s, 1H).

MS-ESI: 385 [M+H]$^+$

Starting material 4 was prepared as follows:—

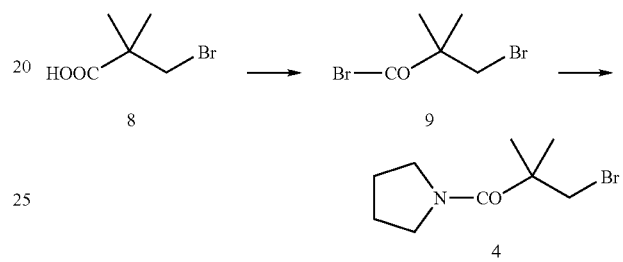

A mixture of 8 (14.48 g; 80 mmol) and oxalyl bromide (43.2 g; 200 mmol) containing one drop of DMF was heated at 50° C. for 2 h and then cooled. The excess of oxalyl bromide was evaporated and the residue azeotroped with toluene to give crude 9 which was taken up directly in $CH_2Cl_2$ (25 ml) and cooled to 0° C. Diisopropylethylamine (14 ml; 80 mmol) was added followed by a solution of pyrrolidine (3.3 ml; 40 mmol) in $CH_2Cl_2$ (30 ml). The mixture was allowed to warm to room temperature overnight and was diluted with $CH_2Cl_2$, washed with aq. HCl (2N), aq. NaOH (1N), water, brine and dried over $MgSO_4$. The residue was purified by flash chromatography eluting with increasingly polar mixtures of EtOAc/CH2Cl2 (5 to 10% EtOAc) to give 4 as a white solid (6.5 g).

Yield: 70%

$^1$H NMR spectrum (DMSO $d_6$): 1.39 (s, 6H); 1.9 (m, 4H); 3.57 (m, 4H); 3.62 (s, 2H)

MS-ESI: 235 [M+H]$^+$

Example 1

3-[2,2-dimethyl-3-oxo-3-(pyrrolidin-1-yl)propoxy]-4-[2-(3-pyridin-4-ylpyrroldin-1-ylcarboxamido) ethyl]-5-(3,5-dimethylphenyl)-1H-pyrazole

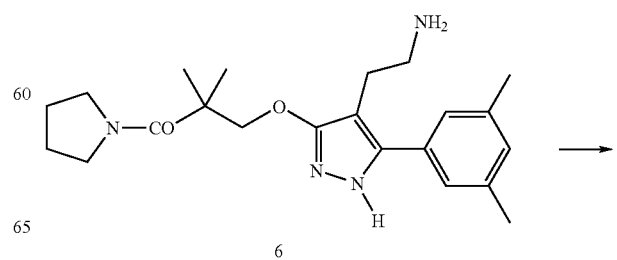

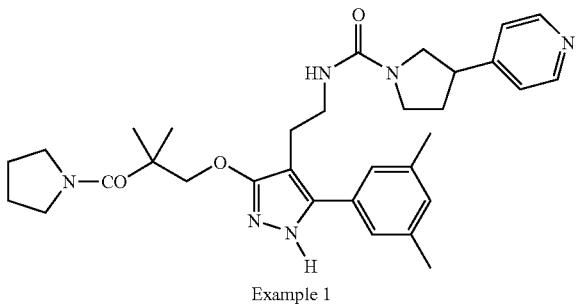

Example 1

A solution of 6 (150 mg; 0.39 mmol) in CH$_2$Cl$_2$ (2 ml) was cooled to 0° C. Diisopropylethylamine (136 ul; 0.78 mmol) was added followed by a solution of 4-nitrophenyl chloroformate (83 mg; 0.41 mmol) in CH$_2$Cl$_2$ (2 ml). The mixture was stirred for 3 h when a solution of 4-(3-pyrrolidyl)-pyridine (70 mg; 0.47 mmol) in CH$_2$Cl$_2$ (2 ml) was added and the mixture was allowed to warm to room temperature overnight. The mixture was directly purified by flash chromatography eluting with increasingly polar mixtures of MeOH/EtOAc (0 to 10% MeOH) to give Example 1 as a beige solid (95 mg).

Yield: 44%

$^1$H NMR spectrum (DMSO d$_6$): 1.29 (s, 6H); 1.75 (m, 4H); 1.95 (m, 1H); 2.2 (m, 1H); 2.31 (s, 6H); 2.56 (m, 2H); 3.1–3.4 (m, 6H); 3.5 (m, 4H); 3.64 (m, 1H); 4.18 (s, 2H); 6.22 (t, 1H); 6.99 (s, 1H); 7.21 (s, 2H); 7.27 (d, 2H); 8.48 (d, 2H).

MS-ESI: 559 [M+H]$^+$

Example 2

[3-2,2-dimethyl-3-oxo-3-pyrrolidin-1-ylpropoxy]-4-2-[(isopropoxycarbonyl)imino(3-pyridin-4-yl-pyrrolidin-1-yl)methyl]aminoethyl]-5-(3,5-dimethylphenyl)-1H-pyrazole

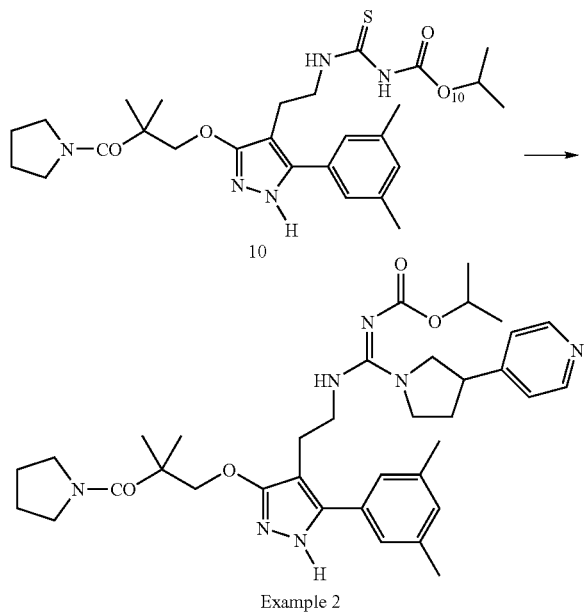

A solution of 10 (260 mg; 0.5 mmol) in CH$_2$Cl$_2$ (5 ml) was cooled to 0° C. EDCI (145 mg; 0.75 mmol) and diisopropylethylamine (130 ul; 0.75 mmol) were added followed by 4-(3-pyrrolidyl)-pyridine (111 mg; 0.75 mmol) and the mixture was allowed to warm to room temperature overnight. The mixture was diluted with CH$_2$Cl$_2$ and the organic phase was washed with sat. aq. NaHCO$_3$, brine and dried over MgSO$_4$. The residue was purified by flash chromatography eluting with increasingly polar mixtures of EtOAc/CH$_2$Cl$_2$ (0 to 100% EtOAc) to give Example 2 as a beige solid (277 mg).

Yield: 86%

$^1$H NMR spectrum (DMSO d$_6$): 1.07 (m, 6H); 1.29 (s, 6H); 1.8 (m, 4H); 1.95 (m, 1H); 2.2 (m, 1H); 2.30 (s, 6H); 2.65 (m, 2H); 3.2–3.4 (m, 6H); 3.5 (m, 4H); 3.65 (m, 1H); 4.18 (s, 2H); 4.6 (m, 1H); 6.95 (m, 1H); 7.00 (s, 1H); 7.12 (s, 2); 7.27 (d, 2H); 8.49 (d, 2H).

MS-ESI: 644 [M+H]$^+$

The starting material 10 was prepared as follows:—

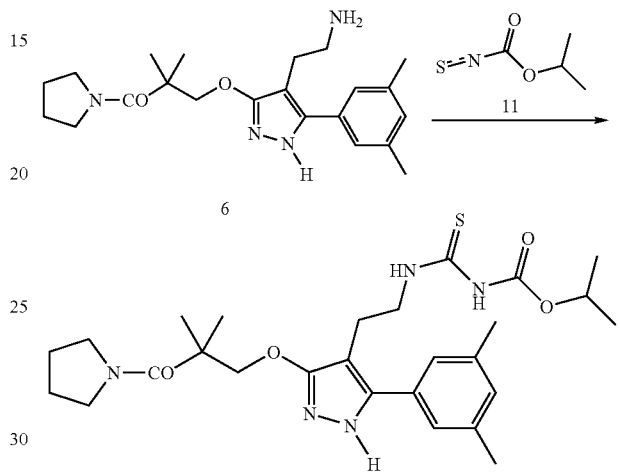

A solution of 6 (200 mg; 0.52 mmol) in CH$_2$Cl$_2$ (2 ml) was cooled to 0° C. A solution of 11 (115 mg; 0.78 mmol) was added and the mixture was allowed to warm to room temperature for 1 h. The mixture was treated with water, diluted with CH$_2$Cl$_2$ and the organic phase was washed with brine and dried over MgSO$_4$. The residue was purified by flash chromatography eluting with increasingly polar mixtures of Et$_2$O/hexanes (0 to 100% Et$_2$O) to give 10 as a beige solid (260 mg).

Yield: 94%

$^1$HNMR spectrum (DMSO d$_6$): 1.22 (m, 6H); 1.31 (s, 6H); 1.8 (m, 4H); 2.32 (s, 6H); 2.71 (m, 2H); 3.5 (m, 4H); 3.74 (m, 2H); 4.20 (s, 2H); 4.83 (m, 1H); 7.02 (s, 1H); 7.17 (s, 2H); 9.89 (t, 1H); 10.81 (s, 1H).

MS-ESI: 530 [M+H]$^+$

Example 3

3-[2,2-dimethyl-3-oxo-3-(N,N-diethylamino)propyl]-4-[2-(-isopropoxycarbonyl)imino(3-pyrid-4-yl-pyrrolidin-1-yl)methyl]aminoethyl]-5-(3,5-dimethylphenyl)-1H-pyrazole

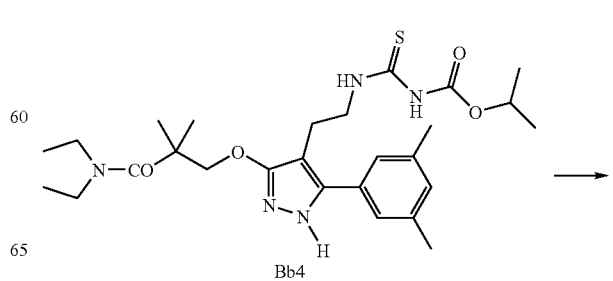

-continued

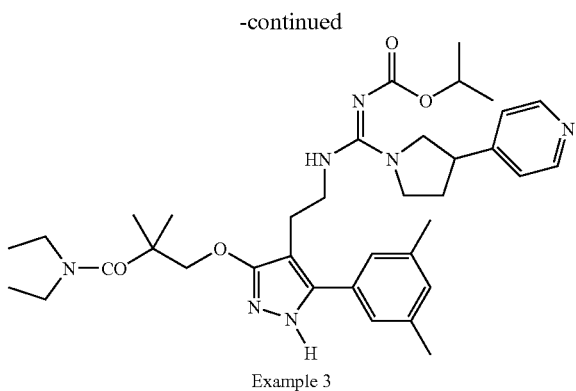

Example 3

A solution of Bb4 (156 mg; 0.29 mmol) in $CH_2Cl_2$ (2 ml) was cooled to 0° C. EDCI (85 mg; 0.44 mmol) and diisopropylethylamine (77 ul; 0.44 mmol) were added followed by 4-(3-pyrrolidyl)-pyridine (56 mg; 0.38 mmol) and the mixture was allowed to warm to room temperature overnight. The mixture was diluted with $CH_2Cl_2$ and the organic phase was washed with sat. aq. $NaHCO_3$, brine and dried over $MgSO_4$. The residue was purified by flash chromatography eluting with increasingly polar mixtures of MeOH/$CH_2Cl_2$ (0 to 100% MeOH) to give Example 3 as a beige solid (180 mg).

Yield: 96%

$^1$H NMR spectrum (DMSO $d_6$): 1.07 (m, 12H);1.31 (s, 6H); 1.93 (m, 1H); 2.23 (m, 1H); 2.30 (s, 6H); 2.65 (m, 2); 3.2–3.55 (m, 10H); 3.57 (m, 1H); 4.17 (s, 2H);4.58 (m, 1H); 6.95 (m, 1H); 7.00 (s, 1H); 7.13 (s, 21); 7.27 (d, 2H); 8.50 (d, 21);11.9 (br s, 11).

MS-ESI: 646 [M+H]$^+$

The starting material Bb4 was prepared as follows:—

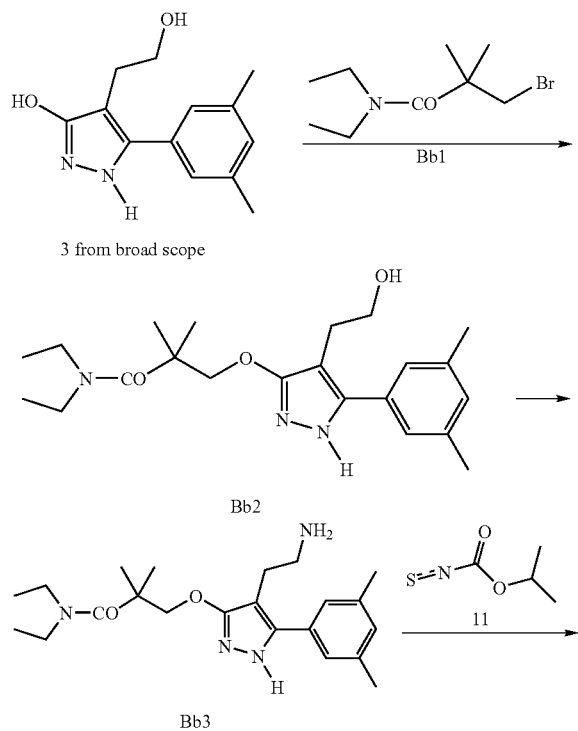

-continued

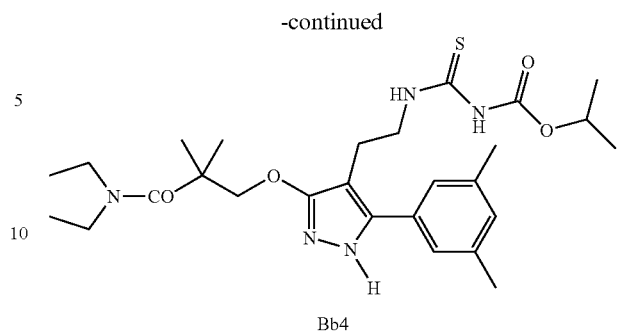

Bb4

A mixture of 3 (1.23 g; 5.3 mmol) and Bb1 (1.32 g; 5.5 mmol) in DMA (20 ml) under argon was treated with $K_2CO_3$ (1.46 g; 10.6 mmol). The mixture was stirred and heated at 70° C. for 2 h. The mixture was poured into sat. aq. $NaHCO_3$, extracted with EtOAc and the organic phase was washed with water, brine and dried over $MgSO_4$. The residue was purified by flash chromatography eluting with increasingly polar mixtures of EtOAc/$CH_2Cl_2$ (0 to 100% EtOAc) to give the alcohol Bb2 as a pale yellow oil (1.92 g).

Yield: 94%

$^1$H NMR spectrum (DMSO $d_4$): 1.08 (t, 6H); 1.32 (s, 6); 2.33 (s, 6H); 2.57 (m, 2H); 3.38 (m, 4H); 3.5 (m, 1H); 4.18 (s, 2H); 4.61 (t, 1H); 7.04 (s, 1H); 7.16 (s, 2H); 11.9 (br s, 1H).

MS-ESI: 388 [M+H]$^+$

A mixture of Bb2 (1.92 g; 4.96 mmol), phthalimide (0.8 g; 5.46 mmol) and triphenylphosphine (5.24 g; 20 mmol) in THF (50 ml) at 0° C. under argon was treated with DEAD (3.2 ml; 20 mmol). The mixture was stirred at this temperature for 2 h when water was added. The mixture was extracted with $Et_2O$ and the organic phase was washed with water, brine and dried over $MgSO_4$.

Evaporation gave a crude solid which, without further purification, was immediately taken up in EtOH (50 ml) and treated with hydrazine hydrate (2.5 ml; 50 mmol). The mixture was stirred for 2 h and then the EtOH was partially evaporated. Addition of $CH_2Cl_2$ caused precipitation of phthalhydrazide which was filtered and rinsed with $CH_2Cl_2$. The filtrate was evaporated and the residue was purified by flash chromatography eluting with increasingly polar mixtures of EtOAc/$CH_2Cl_2$ (0 to 100% EtOAc) to give Bb3 as a beige solid (0.865 g).

Yield: 45%

$^1$H NMR spectrum (DMSO $d_6$): 1.06 (t, 6H); 1.30 (s, 6H); 2.32 (s, 6H); 2.47 (m, 2H); 2.66 (t, 2H); 3.35 (m, 4H); 4.16 (s, 2H); 7.02 (s, 1H); 7.13 (s, 2H); 11.9 (br s, 1H).

MS-ESI: 387 [M+H]$^+$

A solution of Bb3 (210 mg; 0.544 mmol) in $CH_2Cl_2$ (5 ml) was cooled to 0° C. A solution of 11 (120 mg; 0.82 mmol) was added and the mixture was allowed to warm to room temperature for 1 h. The mixture was treated with water, diluted with $CH_2Cl_2$ and the organic phase was washed with brine and dried over $MgSO_4$. The residue was purified by flash chromatography eluting with $CH_2Cl_2$ to give Bb4 as a beige solid (235 mg).

Yield: 81%

$^1$H NMR spectrum (CDCl$_3$): 1.18 (t, 6H); 1.27 (d, 6H); 1.44 (s, 6H); 2.38 (s, 6H); 2.87 (m, 2H); 3.45 (m, 4H); 3.88 (m, 2H); 4.36 (s, 2H); 4.93 (m, 1H); 7.04 (s, 1H); 7.11 (s, 2H); 7.81 (s, 1H); 8.9 (s br, 1H); 9.7 (s, 1H).

MS-ESI: 532 [M+H]$^+$

Starting material Bb1 was prepared as follows:—

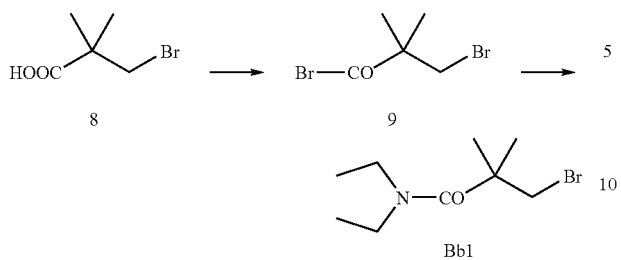

A mixture of 8 (14.48 g; 80 mmol) and oxalyl bromide (43.2 g; 200 mmol) containing one drop of DMF was heated at 50° C. for 2 h and then cooled. The excess of oxalyl bromide was evaporated and the residue azeotroped with toluene to give crude 9 which was taken up directly in $CH_2Cl_2$ (25 ml) and cooled to 0° C. Diisopropylethylamine (14 ml; 80 mmol) was added followed by a solution of pyrrolidine (3.3 ml; 40 mmol) in $CH_2Cl_2$ (30 ml). The mixture was allowed to warm to room temperature overnight and was diluted with $CH_2Cl_2$, washed with aq. HCl (2N), aq. NaOH (1N), water, brine and dried over $MgSO_4$. The residue was purified by flash chromatography eluting with increasingly polar mixtures of EtOAc/$CH_2Cl_2$ (5 to 10% EtOAc) to give Bb1 as a white solid (6.5 g).

Yield: 70%

$^1$H NMR spectrum (DMSO $d_6$): 1.19 (m, 6H); 1.42 (s, 6H); 3.41 (m, 4I); 3.65 (s, 2M)

MS-ESI: 237 $[M+H]^+$

Example 4

3-[2,2-dimethyl-3-oxo-3-(N,N-diethylamino)propyl]-4-[2-(3-pyridin-4-ylpyrrolidin-1-ylcarboxiamido)ethyl]-5-(3,5-dimethylphenyl)-1H-pyrazole

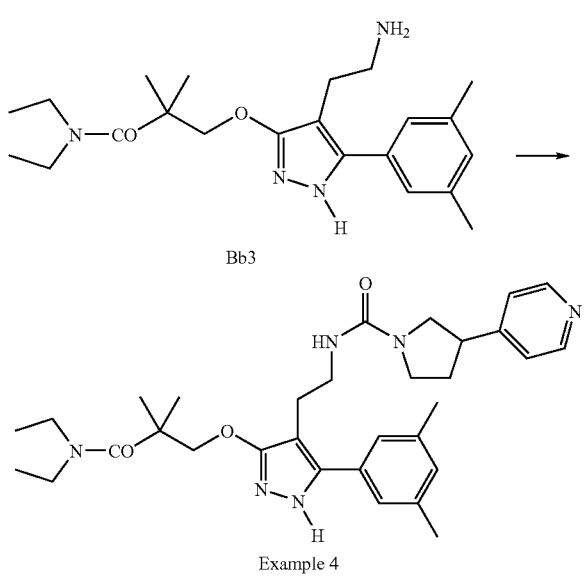

A solution of Bb3 (150 mg; 0.39 mmol) in $CH_2Cl_2$ (2 ml) was cooled to 0° C. Diisopropylethylamine (135 ul; 0.78 mmol) was added followed by a solution of 4-nitrophenyl chloroformate (83 mg; 0.41 mmol) in $CH_2Cl_2$ (2 ml). The mixture was stirred for 3 h when a solution of 4-(3-pyrrolidyl)-pyridine (70 mg; 0.47 mmol) in $CH_2Cl_2$ (2 ml) was added and the mixture was allowed to warm to room temperature overnight. The mixture was directly purified by flash chromatography eluting with increasingly polar mixtures of MeOH/EtOAc (0 to 10% MeOH) to give Example 4 as a beige solid (138 mg).

Yield: 63%

$^1$H NMR spectrum DMSO $d_6$): 1.05; (m, 6H); 1.32 (s, 6H); 1.89 (m, 1H); 2.2 (m, 1H); 2.31 (s, 6H); 2.57 (m, 2); 3.1–3.4 (m, 10H); 3.64 (m, 1H); 4.17 (s, 2H); 6.22 (t, 1H); 6.99 (s, 1H); 7.22 (s, 2H); 7.27 (d, 2H); 8.48 (d, 2H); 11.9 (br s, 1H).

MS-ESI: 561 $[M+H]^+$

Example 5

3-[2,2-dimethyl-3-oxo-3-(7-azabicyclo[2.2.1]heptan-7-yl)propyl]-4-[(1S)-methyl-2[(isopropoxycarbonyl)imino(3-pyrid-4-yl-pyrrolidin-1-yl)methyl]aminoethyl]-5-(3,5-dimethylphenyl)-1H-pyrazole

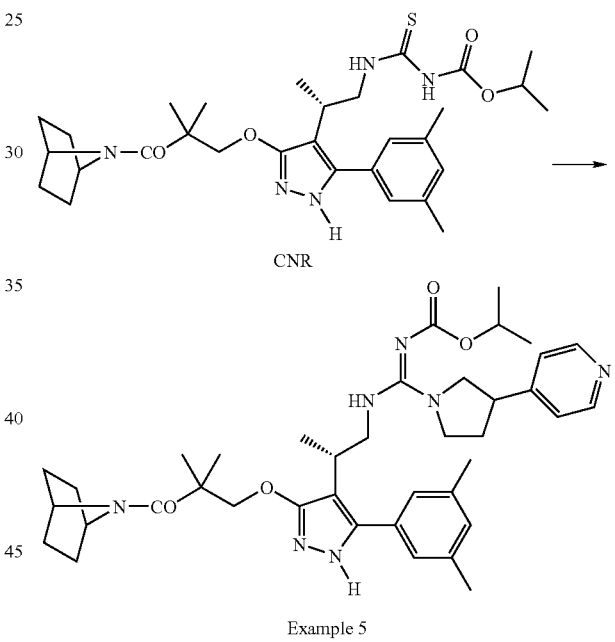

A solution of CNR (141 mg; 0.25 mmol) in $CH_2Cl_2$ (5 ml) was cooled to 0° C. EDCI (72 mg; 0.37 mmol) and diisopropylethylamine (65 ul; 0.37 mmol) were added followed by 4-(3-pyrrolidyl)-pyridine (46 mg; 0.31 mmol) and the mixture was allowed to warm to room temperature overnight. The mixture was diluted with $CH_2Cl_2$ and the organic phase was washed with sat. aq. $NaHCO_3$, brine and dried over $MgSO_4$. The residue was purified by flash chromatography eluting with increasingly polar mixtures of EtOAc/$CH_2Cl_2$ (0 to 100% EtOAc) to give Example 5 as a beige solid (128 mg).

Yield: 78%

$^1$HNMR spectrum (DMSO $d_6$): 1.05 (m, 6H); 1.12 (m, 3H); 1.28 (s, 6H); 1.42 (m, 4I); 1.62 (m, 4H); 1.91 (m, 1H); 2.2 (m, 1H); 2.30 (s, 6I); 2.95 (m, 1H); 3.2-3.7 (m, 7H); 4.17 (s, 2H); 4.56 (m, 3); 7.01 (s, 1H); 7.04 (s, 1H); 7.06 (s, 1H); 7.2 (s br, 1H); 7.27 (dd, 2H); 8.49 (dd, 2H); 11.79 (s, 1H).

MS-ESI: 684 $[M+H]^+$

The starting material CNR was prepared as follows:—

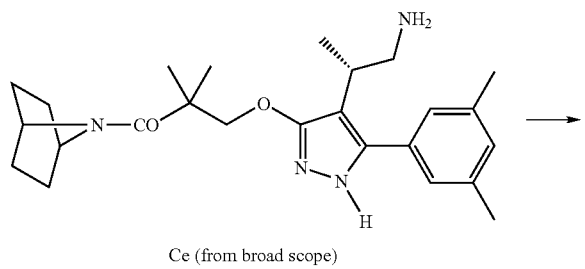

Ce (from broad scope)

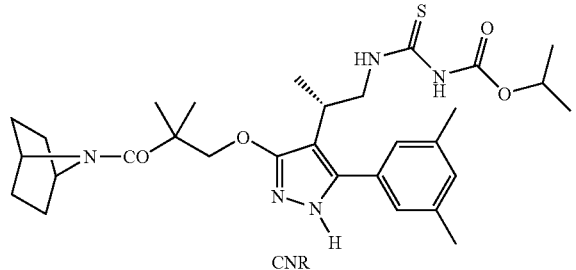

CNR

A solution of Ce (150 mg; 0.35 mmol) in CH$_2$Cl$_2$ (5 ml) was cooled to 0° C. A solution of 11 (77 mg; 0.53 mmol) in CH$_2$Cl$_2$ (1 ml) was added and the mixture was allowed to warm to room temperature for 1 h. The mixture was treated with water, diluted with CH$_2$Cl$_2$ and the organic phase was washed with brine and dried over MgSO$_4$. The residue was purified by flash chromatography eluting with EtOAc/CH$_2$Cl$_2$ (0–20% EtOAc) to give CNR as a gum (141 mg).

Yield: 70%

$^1$H NMR spectrum (DMSO d$_6$): 1.22 (d, 3H); 1.8 (m, 6H); 1.27 (m, 6H);1.41 (m, 4H); 1.61 (m, 4H); 2.29 (s, 6H); 3.06 (q, 1H); 3.65 (m, 1H); 3.84 (m, 1H); 4.19 (m, 2H) 4.58 (s, 2H); 4.79 (m, 1H); 7.02 (s, 1H); 7.04 (s, 2); 9.84 (s, 1H); 11.8 (s br, 1H).

MS-ESI: 570 [M+H]$^+$

Examples 5.1–5.2

The following examples were prepared in a similar manner to Example 5,

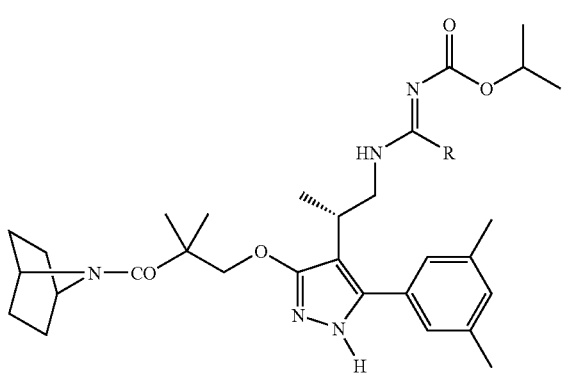

the table shows the R group relating to the above structure, the reaction conditions and characteristics for each example, corresponding to the description of the preparation of Example 5 given above:—

Example 5.1

| R | CNR mg; mmol | Amine mg; mmol | EDCI mg; mmol | DIEA µl; mmol | Mass mg; Yield | MS-ESI |
|---|---|---|---|---|---|---|
| ![structure] | 170; 0.3 | 68; 0.4 | 87; 0.45 | 80; 0.45 | 180; 85% | 705 [M + H]$^+$ |

Chromato.—EtoAc/CH$_2$Cl$_2$ (0 to 100% EtOAc) and then MeOH/CH$_2$Cl$_2$ (0 to 5% MeOH)

$^1$H NMR spectrum (DMSO d(6): 0.9–1.2 (m, 14H); 1.28 (m, 6H); 1.43 (m, 4H); 1.5 (m, 2H); 1.6 (m, 6H); 2.31 (s, 6H); 2.7 (m, 2H); 2.95 (m, 1H); 3.2–3.7 (m, 5H); 3.75 (m, 2H); 3.83 (m, 2H); 4.16 (s, 2H); 4.57 (m, 3H); 7.02 (s, 1H); 7.04 (s, 2H); 7.46 (s br, 1H); 11.80 (s, 1H).

Example 5.2

| R | CNR mg; mmol | Amine mg; mmol | EDCI mg; mmol | DIEA µl; mmol | Mass mg; Yield | MS-ESI |
|---|---|---|---|---|---|---|
| ![structure] | 170; 0.3 | 65; 0.4 | 87; 0.45 | 80; 0.45 | 172; 81% | 698 [M + H]$^+$ |

Chromato.—EtoAc/CH$_2$Cl$_2$ (0 to 100% EtOAc) and then MeOH/CH$_2$Cl$_2$ (0 to 5% MeOH)

$^1$H NMR spectrum (DMSO d$_6$): 1.07 (m, 6H); 1.11 (m, 3H); 1.28 (m, 6H); 1.42 (m, 4H); 1.5 (m, 2H); 1.62 (m, 4H); 1.72 (m, 2H); 2.30 (s, 6H); 2.7 (m, 1H); 2.9 (m, 2H); 2.95 (m, 1H); 3.2–3.4 (m, 2H); 3.85 (m, 2H); 4.17 (m, 2H); 4.57 (m, 3H); 7.01 (s, 1H); 7.06 (s, 2H); 7.18 (d, 2H); 7.5 (s br, 1H); 8.45 (d, 2H); 11.81 (s, 1H).

Example 6

3-[2,2-dimethyl-3-oxo-3-(7-azabicyclo[2.2.1]heptan-7-yl)propoxy]-4-[(1S)-1-methyl-2-(3-pyridin-4-ylpyrrolidin-1-ylcarboxamido)ethyl]-5-(3,5-dimethylphenyl)-1H-pyrazole

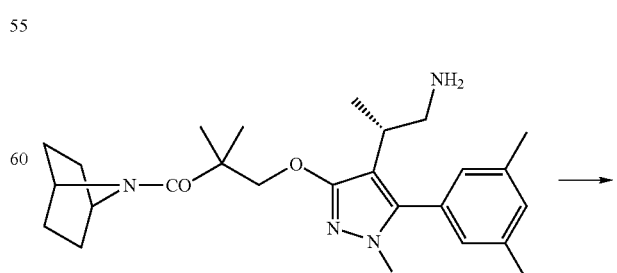

Ce (from broad scope)

-continued

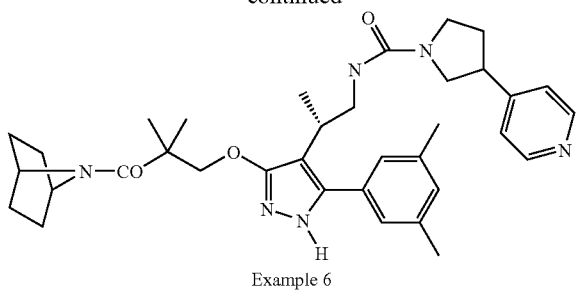

Example 6

A solution of Ce (170 mg; 0.4 mmol) in CH$_2$Cl$_2$ (5 ml) was cooled to 0° C. and DIEA (140 µl; 0.8 mmol) was added. A solution of 4-nitrophenyl chloroformate (85 mg; 0.42 mmol) in CH$_2$Cl$_2$ (1 ml) was added and the mixture was allowed to stir for 30 min. 4-(3-Pyrrolidyl)-pyridine (71 mg; 0.48 mmol) was added and the mixture allowed to warm to room temperature for 1 h. The mixture was directly purified by flash chromatography eluting with MeOH/CH$_2$Cl$_2$ (0–10% MeOH) to give Example 6 as a pale yellow powder (212 mg).

Yield: 88%

$^1$H NMR spectrum (DMSO d$_6$): 1.11 (m, 3H); 1.28 (m, 6H); 1.42 (m, 4H); 1.62 (m, 4H); 1.95 (m, 1H); 2.22 (m, 1H); 2.29 (s, 6H); 2.93 (m, 1H); 3.2–3.7 (m, 6H); 3.67 (m, 1H); 4.17 (s, 2H); 4.58 (s, 2H); 6.21 (m, 1H); 7.00 (s, 1H); 7.14 (s, 2H); 7.26 (m, 2H); 8.47 (m, 2H); 11.79 (s, 1H).

MS-ESI: 599 [M+H]$^+$

Examples 6.1–6

The following examples were prepared in a similar manner to Example 6,

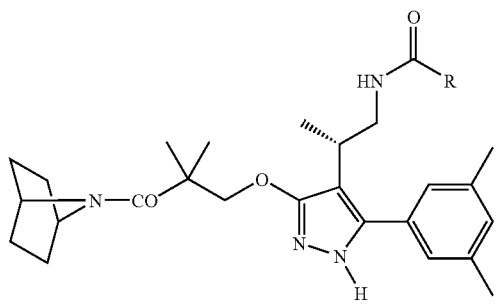

the table shows the R group relating to the above structure, the reaction conditions and characteristics for each example, corresponding to the description of the preparation of Example 6 given above:—

Example 6.1

| R | Ce mg; mmol | DIEA µl; mmol | 4-NPC mg; mmol | Amine mg; mmol | Mass mg; Yield | MS-ESI |
|---|---|---|---|---|---|---|
| | 170; 0.4 | 140; 0.8 | 90; 0.42 | 71; 0.48 | 226; 94% | 599 [M + H]$^+$ |

Chromato.—MeOH/EtoAc (0 to 5% MeOH)

$^1$H NMR spectrum (DMSO d$_6$): 1.11 (m, 3H); 1.28 (m, 6H); 1.42 (m, 4H); 1.62 (m, 4H); 1.99 (m, 1H); 2.20 (m, 1H); 2.29 (s, 6H); 2.93 (m, 1H); 3.2–3.5 (m, 6H); 3.68 (m, 1H); 4.17 (s, 2H); 4.58 (s, 2H); 6.15 (m, 1H); 7.00 (s, 1H); 7.14 (m, 2H); 7.24 (m, 1H); 7.29 (m, 1H); 7.72 (m, 1H); 8.49 (m, 1H); 11.74 (s, 1H).

Example 6.2

| R | Ce mg; mmol | DIEA µl; mmol | 4-NPC mg; mmol | Amine mg; mmol | Mass mg; Yield | MS-ESI |
|---|---|---|---|---|---|---|
| | 110; 0.26 | 90; 0.52 | 55; 0.27 | 52; 0.28 | 131; 81% | 620 [M + H]$^+$ |

Chromato.—EtoAc/CH$_2$Cl$_2$ (0 to 100% EtOAc)

$^1$HNMR spectrum (DMSO d$_6$): 0.9 (m, 2H); 1.07 (m, 3H); 1.14 (m, 4H); 1.28 (m, 6H); 1.4–1.7 (m, 12H); 2.30 (s, 6H); 2.9 (m, 1H); 3.2–3.4 (m, 6H); 3.82 (m, 2H); 3.96 (m, 2H); 4.17 (m, 2H); 4.58 (m, 2H); 6.45 (m, 1H); 6.99 (s, 1H); 7.14 (s, 2H); 11.81 (s, 1H).

Therapeutic Uses

Compounds of Formula (I) are provided as medicaments for antagonising gonadotropin releasing hormone (GnRH) activity in a patient, eg, in men and/or women. To this end, a compound of Formula (I) can be provided as part of a pharmaceutical formulation which also includes a pharmaceutically acceptable diluent or carrier (eg, water). The formulation may be in the form of tablets, capsules, granules, powders, syrups, emulsions (eg, lipid emulsions), suppositories, ointments, creams, drops, suspensions (eg, aqueous or oily suspensions) or solutions (eg, aqueous or oily solutions). If desired, the formulation may include one or more additional substances independently selected from stabilising agents, wetting agents, emulsifying agents, buffers, lactose, sialic acid, magnesium stearate, terra alba, sucrose, corn starch, talc, gelatin, agar, pectin, peanut oil, olive oil, cacao butter and ethylene glycol.

The compound is preferably orally administered to a patient, but other routes of administration are possible, such as parenteral or rectal administration. For intravenous, subcutaneous or intramuscular administration, the patient may receive a daily dose of 0.1 mgkg$^{-1}$ to 30 mgkg$^{-1}$ (preferably, 5 mgkg$^{-1}$ to 20 mgkg$^{-1}$) of the compound, the compound being administered 1 to 4 times per day. The intravenous, subcutaneous and intramuscular dose may be given by means of a bolus injection. Alternatively, the intravenous dose may be given by continuous infusion over a period of time. Alternatively, the patient may receive a daily oral dose which is approximately equivalent to the daily parenteral dose, the composition being administered 1 to 4 times per day. A suitable pharmaceutical formulation is one suitable for oral administration in unit dosage form, for example as a tablet or capsule, which contains between 10 mg and 1 g (preferably, 100 mg and 1 g) of the compound of the invention.

Buffers, pharmaceutically acceptable co-solvents (eg, polyethylene glycol, propylene glycol, glycerol or EtOH) or complexing agents such as hydroxy-propyl β cyclodextrin may be used to aid formulation.

One aspect of the invention relates to the use of compounds according to the invention for reducing the secretion of LH and/or FSH by the pituitary gland of a patient. In this respect, the reduction may be by way of a reduction in biosynthesis of the LH and FSH and/or a reduction in the release of LH and FSH by the pituitary gland. Thus, compounds according to the invention can be used for therapeutically treating and/or preventing a sex hormone related condition in the patient. By "preventing" we mean reducing the patient's risk of contracting the condition. By "treating" we mean eradicating the condition or reducing its severity in the patient. Examples of sex hormone related conditions are: a sex hormone dependent cancer, benign prostatic hypertrophy, myoma of the uterus, endometriosis, polycystic ovarian disease, uterine fibroids, prostatauxe, myoma uteri, hirsutism and precocious puberty. Examples of sex hormone dependent cancers are: prostatic cancer, uterine cancer, breast cancer and pituitary gonadotrophe adenoma.

The compounds of the invention may be used in combination with other drugs and therapies used to treat/prevent sex-hormone related conditions.

If formulated as a fixed dose such combination products employ the compounds of this invention within the dosage range described herein and the other pharmaceutically-active agent within its approved dosage range. Sequential use is contemplated when a combination formulation is inappropriate.

In the field of medical oncology examples of such combinations include combinations with the following categories of therapeutic agent:

i) anti-angiogenic agents (for example linomide, inhibitors of integrin αvβ3 function, angiostatin, endostatin, razoxin, thalidomide) and including vascular endothelial growth factor (VEGF) receptor tyrosine kinase inhibitors (RTKIs) (for example those described in international patent applications publication nos. WO-97/22596, WO-97/30035, WO-97/32856 and WO-98/13354, the entire disclosure of which documents is incorporated herein by reference);

ii) cytostatic agents such as anti-oestrogens (for example tamoxifen, toremifene, raloxifene, droloxifene, iodoxyfene), progestogens (for example megestrol acetate), aromatase inhibitors (for example anastrozole, letrozole, vorazole, exemestane), anti-progestogens, anti-androgens (for example flutamide, nilutamide, bicalutamide, cyproterone acetate), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example epidermal growth factor EGF), platelet derived growth factor and hepatocyte growth factor such inhibitors include growth factor antibodies, growth factor receptor antibodies, tyrosine kinase inhibitors and serine/threonine kinase inhibitors);

iii) biological response modifiers (for example interferon);

iv) antibodies (for example edrecolomab); and v) anti-proliferative/anti-neoplastic drugs and combinations thereof, as used in medical oncology, such as anti-metabolites (for example anti-folates like methotrexate, fluoropyrimidines like 5-fluorouracil, purine and adenosine analogues, cytosine arabinoside); anti-tumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); anti-mitotic agents (for example vinca alkaloids like vincristine and taxoids like taxol, taxotere); enzymes (for example asparaginase); thymidylate synthase inhibitors (for example raltitrexed); topoisomerase inhibitors (for example epipodophyllotoxins like etoposide and teniposide, amsacrine, topotecan, irinotecan).

The compounds of the invention may also be used in combination with surgery or radiotherapy.

Assays

The ability of compounds according to the invention to act as antagonists of GnRH can be determined using the following in vitro assays.

Binding Assay Using Rat pituitary GnRH Receptor

The assay is performed as follows:—

1. Incubate crude plasma membranes prepared from rat pituitary tissues in a Tris.HCl buffer (pH. 7.5, 50 mM) containing bovine serum albumin (0.1%), [I-125]D-t-Bu-Ser6-Pro9-ethyl amide-GnRH, and the test compound. Incubation is at 4° C. for 90 minutes to 2 hours.
2. Rapidly filter and repeatedly wash through a glass fibre filter.
3. Determine the radioactivity of membrane bound radio-ligands using a gamma counter.

From this data, the $IC_{50}$ of the test compound can be determined as the concentration of the compound required to inhibit radio-ligand binding to GnRH receptors by 50%. Compounds according to the present invention have activity at a concentration from 1 nM to 5 μM.

Binding Assay Using Human GnRH Receptor

Crude membranes prepared from CHO cells expressing human GnRH receptors are sources for the GnRH receptor. The binding activity of compounds according to the invention can be determined as an $IC_{50}$ which is the compound concentration required to inhibit the specific binding of [$^{125}$I]buserelin to GnRH receptors by 50%. [$^{125}$I]Buserelin (a peptide GnRH analogue) is used here as a radiolabelled ligand of the receptor.

Assay to Determine Inhibition of LH release

The LH release assay can be used to demonstrate antagonist activity of compounds, as demonstrated by a reduction in GnRH-induced LH release.

Preparation of Pituitary Glands

Pituitary glands obtained from rats are prepared as follows. Suitable rats are Wistar male rats (150–200 g) which have been maintained at a constant temperature (eg, 25° C.) on a 12 hour light/12 hour dark cycle. The rats are sacrificed by decapitation before the pituitary glands are aseptically removed to tube containing Hank's Balanced Salt Solution (HBSS). The glands are further processed by:—

1. Centrifugation at 250×g for 5 minutes;
2. Aspiration of the HBSS solution;
3. Transfer of the glands to a petri dish before mincing with a scalpel;
4. Transfer of the minced tissue to a centrifuge tube by suspending the tissue three successive times in 10 ml aliquots of HBSS containing 0.2% collagenase and 0.2% hyaluronidase;
5. Cell dispersion by gentle stirring of the tissue suspension while the tube is kept in a water bath at 37° C.;
6. Aspiration 20 to 30 times using a pipette, undigested pituitary fragments being allowed to settle for 3 to 5 minutes;
7. Aspiration of the suspended cells followed by centrifugation at 1200×g for 5 minutes;

Testing of Compounds

The test compound is dissolved in DMSO to a final concentration of 0.5% in the incubation medium.

1.5 hours prior to the assay, the cells are washed three times with DMEM containing 0.37% $NaHCO_3$, 10% horse serum, 2.5% foetal bovine serum, 1% non essential amino acids (100×), 1% glutamine (100×), 1% penicillin/streptomycin (10,000 units of each per ml) and 25 mM HEPES at pH 7.4. Immediately prior to the assay, the cells are again washed twice in this medium.

Following this, 1 ml of fresh medium containing the test compound and 2 nM GnRH is added to two wells. For other test compounds (where it is desired to test more than one compound), these are added to other respective duplicate wells. Incubation is then carried out at 37° C. for three hours.

Following incubation, each well is analysed by removing the medium from the well and centrifuging the medium at 2000×g for 15 minutes to remove any cellular material. The supernatant is removed and assayed for LH content using a double antibody radio-immuno assay. Comparison with a suitable control (no test compound) is used to determine whether the test compound reduces LH release. Compounds according to the present invention have activity at a concentration from 1 nM to 5 μM.

8. Re-suspension of the cells in culture medium of DMEM containing 0.37% $NaHCO_3$, 10% horse serum, 2.5% foetal bovine serum, 1% non essential amino acids, 1% glutamine and 0.1% gentamycin;
9. Treatment of the undigested pituitary fragments 3 times with 30 ml aliquots of the collagenase and hyaluronidase;
10. Pooling of the cell suspensions and dilution to a concentration of 3×10 cells/ml;
11. Placing of 11.0 ml of this suspension in each of a 24 well tray, with the cells being maintained in a humidified 5% $CO_2$/95% air atmosphere at 37° C. for 3 to 4 days

The invention claimed is:

1. A compound of Formula (I),

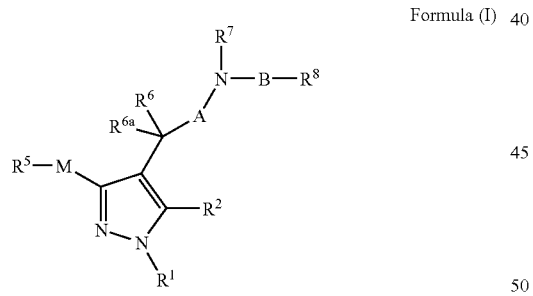

Formula (I)

wherein

A represents a direct bond or optionally substituted $C_{1-5}$alkylene;

B is a group of Formula (II):

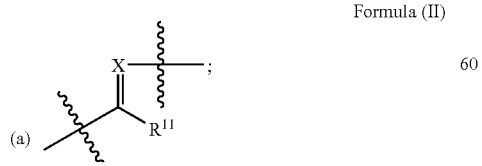

Formula (II)

wherein at position (a) Formula (II) is attached to the nitrogen atom and the group X is attached to $R^8$;

M is $-(CH_2)_{0-2}-O-$;

$R^1$ represents hydrogen; optionally substituted $C_{1-8}$alkyl; or $(CH_2)_b-R^a$, wherein $R^a$ represents $C_{3-8}$cycloalkyl and b is zero or an integer from 1 to 6;

$R^2$ represents an optionally substituted mono- or bi-cyclic aromatic ring structure wherein the optional substituents are selected from cyano, $NR^3R^{3a}$, optionally substituted $C_{1-8}$alkyl, optionally substituted $C_{1-8}$alkoxy or halo;

$R^3$ and $R^{3a}$ are independently selected from hydrogen; optionally substituted $C_{1-8}$alkyl and optionally substituted aryl;

$R^5$ is selected from an optionally substituted 3 to 8 membered heterocyclic ring containing from 1 to 4 heteroatoms independently selected from O, N and S; or a group of formula III-a; III-b; III-c; III-d; III-e; III-f, III-g, III-h, III-i or III-j:

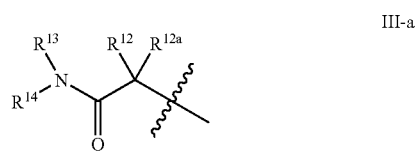

III-a

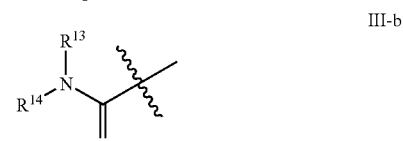

III-b

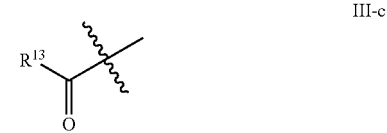

III-c

III-d

III-e

III-f

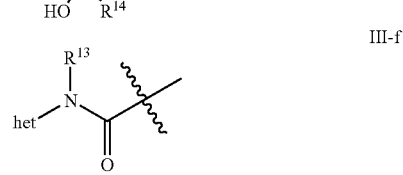

III-g

III-h

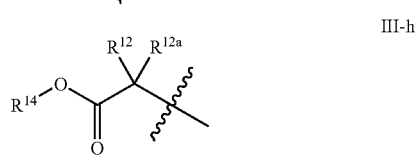

-continued

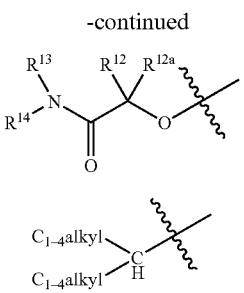

III-i

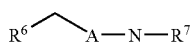

III-j wherein het represents an optionally substituted 3 to 8 membered heterocyclic ring containing from 1 to 4 heteroatoms independently selected from O, N and S;
$R^6$ and $R^{6a}$, are independently selected from hydrogen and optionally substituted $C_{1-8}$alkyl; or $R^6$ and $R^{6a}$ together represent carbonyl;
$R^7$ represents hydrogen or optionally substituted $C_{1-8}$alkyl;
or $$R^6 \diagup A{-}N{-}R^7$$

together from an optionally substituted 3- to 8-membered heterocyclic ring containing from 1 to 3 further heteroatoms independently selected from O, N and S, and $R^6$a represents hydrogen or optionally substituted $C_{1-8}$alkyl;
X and $R^8$ are selected from:
(i) X represents N and $R^8$ is selected from:
cyano, hydrogen, hydroxy, —O—$R^b$, —$NR^bR^c$—C(O) O—$R^b$, —$CONR^bR^c$ or NH—C(O)—$R^b$, where $R^b$ and $R^c$ are independently selected from hydrogen and $C_{1-4}$alkyl optionally substituted with hydroxy, amino, N—$C_{1-4}$alkylamino, N,N-di-$C_{1-4}$alkylamino, HO—$C_{2-4}$alkyl-NH— or HO—$C_{2-4}$alkyl-N($C_{1-4}$alkyl)-;
(ii) X represents CH and $R^8$ represents $NO_2$; and
(iii) X—$R^8$ represents —O—;
$R^{11}$ is a group of the formula: $N(R^9R^{10})$ wherein $R^9$ represents hydrogen, optionally substituted aryl, an optionally substituted 3- to 10 membered heterocyclic ring or optionally-substituted $C_{1-8}$alkyl and $R^{10}$ represents hydrogen or optionally substituted $C_{1-8}$alkyl; or
the structure $N(R^9R^{10})$ represents an optionally-substituted 3- to 10 membered heterocyclic ring optionally containing from 1 to 3 further heteroatoms independently selected from O, N and S;
$R^{12}$ and $R^{12a}$ are independently selected from hydrogen or optionally substituted $C_{1-8}$alkyl; or $R^{12}$ and $R^{12a}$ together with the carbon to which they are attached form an optionally substituted 3 to 7-membered cycloalkyl ring;
$R^{13}$ and $R^{14}$ are selected from:
(i) $R^{13}$ is selected from hydrogen; optionally substituted $C_{1-8}$alkyl; optionally substituted aryl; —$R^d$—Ar, where $R^d$ represents $C_{1-8}$alkylene and Ar represents optionally substituted aryl; and optionally substituted 3 to 8 membered heterocyclic ring optionally containing from 1 to 3 further heteroatoms independently selected from O, N and S; and $R^{14}$ is selected from hydrogen; optionally substituted $C_{1-8}$alkyl and optionally substituted aryl;
(ii) where $R^5$ represents a group of formula III-a, III-b or III-i, then the group $NR^{13}$(—$R^{14}$) represents an optionally substituted 3 to 8 membered heterocyclic ring optionally containing from 1 to 3 further heteroatoms independently selected from O, N and S; or
(iii) where $R^5$ represents structure III-e, then the group

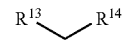

represents an optionally substituted 3 to 8 membered heterocyclic ring optionally containing from 1 to 4 heteroatoms independently selected from O, N and S;
or a salt, pro-drug or solvate thereof.

2. A compound according to claim 1 wherein $R^9$ represents hydrogen, optionally substituted aryl, an optionally substituted 3- to 10 membered heterocyclic ring or optionally-substituted $C_{1-8}$alkyl and
$R^{10}$ represents hydrogen or optionally substituted $C_{1-8}$alkyl wherein the optional substituents on aryl, the heterocyclic ring and $C_{1-8}$alkyl are selected from: hydroxy, amino, nitro, cyano, optionally-substituted aryl, optionally substituted 3 to 8 membered heterocyclyl containing from 1 to 4 heteroatoms independently selected from O, N and S, —O—$R^b$, C(O)$NR^bR^c$, —$NR^bR^c$, —$NR^cC(O)$—$R^b$, —C(O)$NR^bR^c$, —$NR^cS(O_{0-2})R^b$ and —$S(O_{0-2})R^b$, wherein $R^b$ and $R^c$ are as defined in claim 1.

3. A compound according to claim 2 wherein $R^9$ is a $C_{1-6}$alkyl group substituted by pyridyl, thienyl, piperidinyl, imidazolyl, triazolyl, thiazolyl, pyrrolidinyl, piperazinyl, morpholinyl, imidazolinyl, benztriazolyl, benzimidazolyl, pyrimidinyl, pyrazinyl, pyridazinyl, oxazolyl, furanyl, pyrrolyl, 1,3-dioxolanyl or 2-azetinyl, each of which is optionally substituted.

4. A compound according to claim 1 wherein the structure $N(R^9R^{10})$ represents an optionally-substituted 3- to 10 membered heterocyclic ring optionally containing from 1 to 3 further heteroatoms independently selected from O, N and S.

5. A compound according to claim 4 wherein the 3- to 10 membered heterocyclic ring is optionally substituted by one of more groups selected from $R^{15}$ wherein $R^{15}$ is selected from optionally substituted aryl, an optionally substituted 3 to 10 membered heterocyclic ring or optionally substituted $C_{1-4}$alkyl wherein the optional substituents on aryl, a heterocyclic ring or $C_{1-4}$alkyl are selected from: hydroxy, amino, nitro, cyano, optionally-substituted aryl, optionally substituted 3 to 8 membered heterocyclyl containing from 1 to 4 heteroatoms independently selected from O, N and S, —O—$R^b$, C(O)$NR^bR^c$, —$NR^bR^c$, —$NR^cC(O)$—$R^b$, —C(O)$NR^bR^c$, —$NR^cS(O_{0-2})R^b$ and —$S(O_{0-2})R^b$, wherein $R^b$ and $R^c$ are independently selected from hydrogen and $C_{1-4}$alkyl optionally substituted with hydroxy, amino, N—$C_{1-4}$alkylamino, N,N-di-$C_{1-4}$alkylamino, HO—$C_{2-4}$alkyl-NH— or HO—$C_{2-4}$alkyl-N($C_{1-4}$alkyl)-.

6. A compound according to claim 1 wherein $R^5$ is selected from a group of formula III-a, III-g, III-h, III-i or III-j:

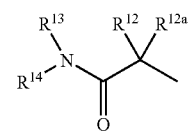

III-a

-continued

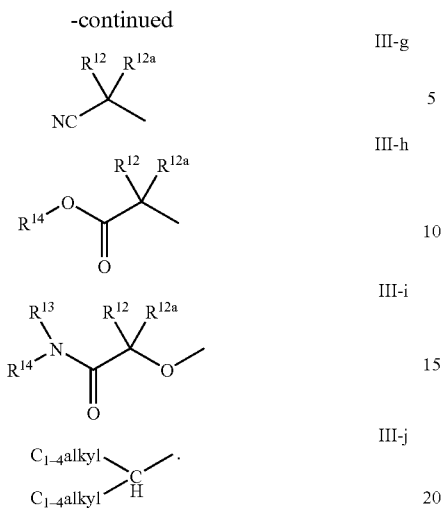

7. A compound according to claim 1 wherein X and $R^8$ are selected from
   (a) X represents N and $R^8$ represents cyano or —C(O)O—$R^b$; or
   (b) X represents N and $R^8$ represents hydrogen.

8. A compound according to claim 1 wherein $R^2$ is selected from an optionally substituted monocyclic aromatic ring structure wherein the optional substituents are selected from cyano, $NR^3R^{3a}$, optionally substituted $C_{1-8}$alkyl, optionally substituted $C_{1-8}$alkoxy or halo wherein $R^3$ and $R^{3a}$ are independently selected from hydrogen, $C_{1-6}$alkyl or aryl.

9. A compound according to claim 1 wherein $R^1$ is hydrogen.

10. The compound:
   3-[2,2-dimethyl-3-oxo-3-(7-azabicyclo[2.2.1]heptan-7-yl)propoxy]-4-[(1S)-1-methyl-2-[(isopropoxycarbonyl)imino(-3-pyridin-4-yl-pyrrolidin-1-yl)methyl]aminoethyl]-5-(3,5-dimethylphenyl)-1H-pyrazole;
or a salt, pro-drug or solvate thereof.

11. A pharmaceutical formulation comprising a compound, or salt, pro-drug or solvate thereof, according to claim 1 and a pharmaceutically acceptable diluent or carrier.

12. A process of producing a compound, or salt, pro-drug or solvate thereof, according to claim 1, wherein the process comprises a reaction step selected from any one of steps (a) to (f):—
   (a) for compounds wherein X is N and $R^8$ is CN, reaction of a compound of formula XXXII as follows

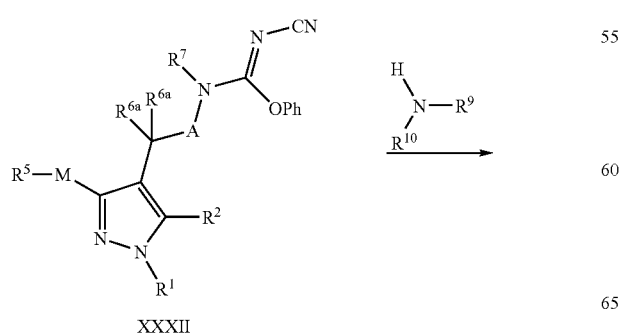

XXXII

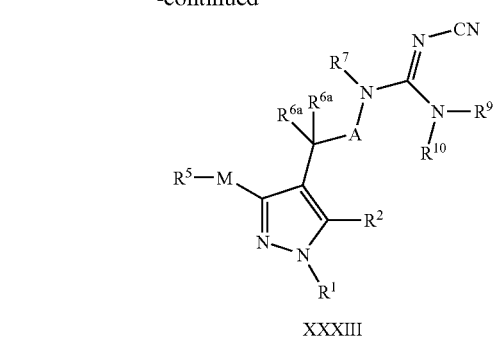

XXXIII (b) for compounds wherein X is N and $R^8$ is hydrogen, cleavage of the cyano group of compound of formula XXXIII in the presence of acid to produce compound of formula XXXIV

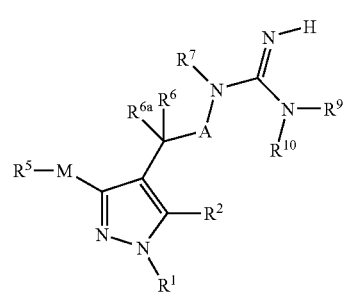

XXXIV (c) for compounds wherein X is CH and $R^8$ is $NO_2$, reaction of compound of formula XXXV as follows

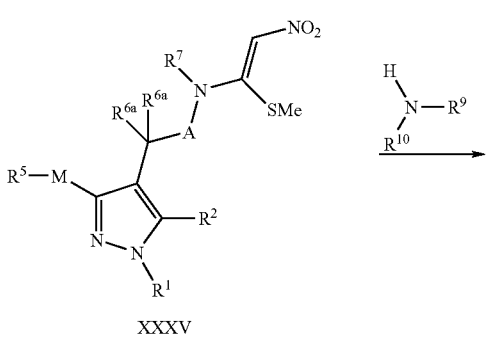

XXXV

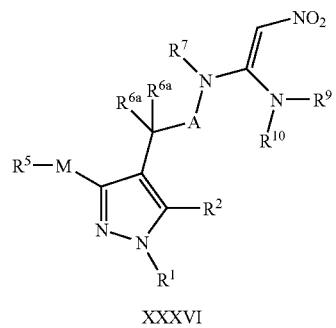

XXXVI (d) for compounds where X—R⁸ is O, reaction of compound of formula XXXVII as follows

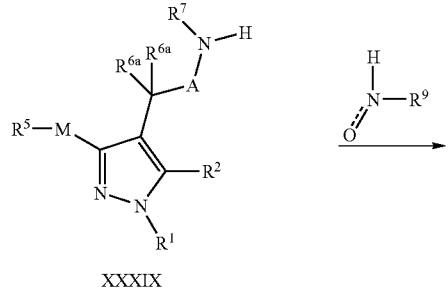

XXXIX

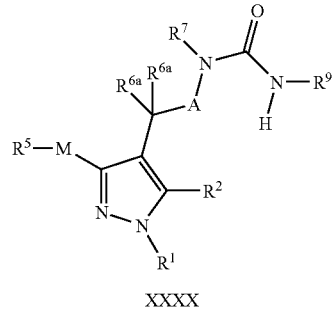

XXXX (e) for compounds where X—R⁸ is O, reaction of compound of formula XXXIX as follows

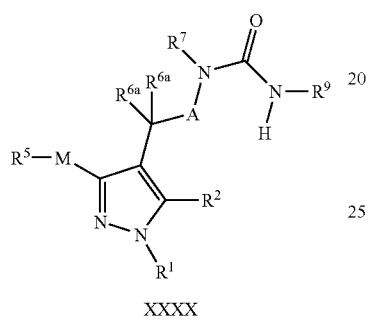

XXXX

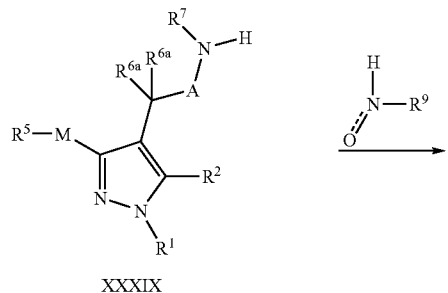

XXXIX (f) to form a compound wherein X is nitrogen reaction of a compound of formula XXXXI as follows

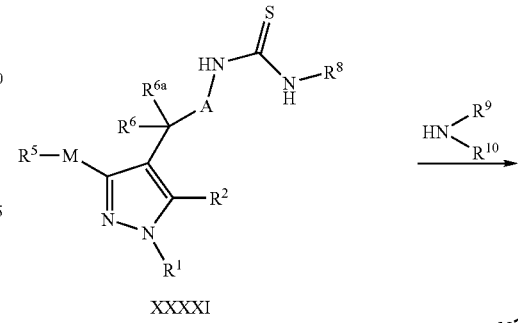

XXXXI

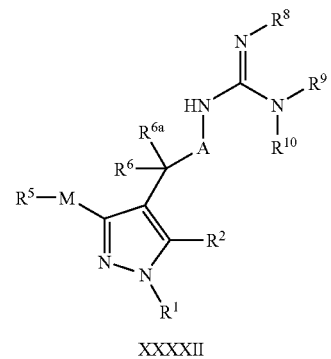

XXXXII and thereafter if necessary:
i) converting a compound of the Formula (I) into another compound of the Formula (I);
ii) removing any protecting groups;
iii) forming a salt, pro-drug or solvate.

* * * * *